(12) United States Patent
Sundaram

(10) Patent No.: US 11,918,622 B2
(45) Date of Patent: *Mar. 5, 2024

(54) READY-TO-USE BIVALIRUDIN COMPOSITIONS

(71) Applicant: MAIA Pharmaceuticals, Inc., Princeton, NJ (US)

(72) Inventor: Srikanth Sundaram, Somerset, NJ (US)

(73) Assignee: MAIA PHARMACEUTICALS, INC., Princeton, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/060,529

(22) Filed: Nov. 30, 2022

(65) Prior Publication Data

US 2023/0293626 A1    Sep. 21, 2023

Related U.S. Application Data

(63) Continuation of application No. 16/417,362, filed on May 20, 2019.

(51) Int. Cl.

| | | |
|---|---|---|
| *A61K 38/10* | (2006.01) | |
| *A61K 9/00* | (2006.01) | |
| *A61K 38/58* | (2006.01) | |
| *A61K 47/02* | (2006.01) | |
| *A61K 47/10* | (2017.01) | |
| *A61P 7/02* | (2006.01) | |
| *A61K 47/12* | (2006.01) | |
| *A61K 47/18* | (2017.01) | |

(52) U.S. Cl.
CPC ............ *A61K 38/10* (2013.01); *A61K 9/0019* (2013.01); *A61K 38/58* (2013.01); *A61K 47/02* (2013.01); *A61K 47/10* (2013.01); *A61P 7/02* (2018.01); *A61K 47/12* (2013.01); *A61K 47/183* (2013.01)

(58) Field of Classification Search
None
See application file for complete search history.

(56) References Cited

U.S. PATENT DOCUMENTS

| | | |
|---|---|---|
| 5,196,404 A | 3/1993 | Maraganore et al. |
| 5,240,913 A | 8/1993 | Maraganore et al. |
| 5,425,936 A | 6/1995 | Maraganore et al. |
| 5,433,940 A | 7/1995 | Maraganore et al. |
| 5,691,311 A | 11/1997 | Maraganore et al. |
| 6,274,553 B1 | 8/2001 | Furuya et al. |
| 7,144,861 B2 | 12/2006 | Chang et al. |
| 7,582,727 B1 | 9/2009 | Krishna et al. |
| 7,598,343 B1 | 10/2009 | Krishna et al. |
| 7,713,928 B1 | 5/2010 | Palepu et al. |
| 7,803,762 B1 | 9/2010 | Palepu et al. |
| 7,985,733 B1 | 7/2011 | Motheram |
| 8,512,691 B2 | 8/2013 | Dibiase et al. |
| 8,932,574 B2 | 1/2015 | Dibiase et al. |
| 9,522,174 B2 | 12/2016 | Dibiase et al. |
| 9,879,067 B2 | 1/2018 | Oliver et al. |
| 2007/0093423 A1 | 4/2007 | Tovi et al. |
| 2011/0046063 A1 | 2/2011 | Palepu et al. |
| 2015/0328317 A1 | 11/2015 | Chen et al. |
| 2016/0106840 A1 | 4/2016 | Chen et al. |
| 2016/0296622 A1 | 10/2016 | Sundaram |
| 2017/0224789 A1 | 8/2017 | Sonavaria et al. |
| 2020/0368311 A1* | 11/2020 | Sundaram ............ A61K 9/0019 |

FOREIGN PATENT DOCUMENTS

| | | |
|---|---|---|
| CN | 101244043 A | 8/2008 |
| WO | 2008134601 A1 | 11/2008 |
| WO | 2009015028 A1 | 1/2009 |
| WO | 2009042139 A1 | 4/2009 |
| WO | 2009086062 A1 | 7/2009 |

OTHER PUBLICATIONS

FDA Guidance for Industry, Statistical Approaches to Establishing Bioequivalence, (2001), (48 pages).
International Search Report and Written Opinion with Respect to PCT/US2019/033139 dated Aug. 19, 2019.
Allie, "Commentary: Dethrombosing Strategies and Endopharmacologic and Mechanical Techniques", Vasc. Dis. Manag., (2006) 3(3):368-75 https://www.vasculardiseasemanagement.com/content/commentary-dethrombosing-strategies-and-endooharmacoloaic-and-mechanical-techniques.
Goolcharran and Borchardt, "Kinetics of Diketopiperazine Formation Using Model Peptides", J. Pharma. Sci., (1998) 87(3):283-288.
Li, et al., "Effects of Solution Polarity and Viscosity on Peptide Deamidation", J. Peptide Res., (2000) 56:326-334.
Money, Nicholas P, "Osmotic Pressure of Aqueous Polyethylene Glycols", Plant Physiol., (1989) 91 :766-769.
Oliyai and Borchardt, "Chemical Pathways of Peptide Degradation. IV. Pathways, Kinetics, and Mechanism of Degradation of an Aspartyl Residue in a Model Hexapeptide", J. Pharma. Res., (1993) 10(1):95-102.
Wakankar and Borchardt, "Formulation Considerations for Proteins Susceptible to Asparagine Deamidation and Asoartate Isomerization", J. Pharma. Sci., (2006) 95(11 ):2321-2336.
Wang, Wei, "Tolerability of Hypertonic Injectables", Int Journal of Pharmaceutics, (2015) 490:308-315.
Zupancic, et al., "Storage stability of bivalirudin: hydrophilic versus lipophilic solutions", Journal of Pharmaceutical Sciences v106 2017 pp. 1322-1330) (Year: 2017).

* cited by examiner

*Primary Examiner* — Ronald T Niebauer
(74) *Attorney, Agent, or Firm* — Blank Rome LLP

(57) ABSTRACT

Ready-to-use liquid bivalirudin compositions, methods of using the ready-to-use bivalirudin compositions, and methods of preparing the ready-to-use liquid bivalirudin compositions are provided herein. The liquid ready-to-use bivalirudin compositions comprise a pharmaceutically acceptable amount of bivalirudin.

21 Claims, No Drawings
Specification includes a Sequence Listing.

SEQUENCE LISTING

```
Sequence total quantity: 6
SEQ ID NO: 1            moltype = AA  length = 20
FEATURE                 Location/Qualifiers
source                  1..20
                        mol_type = protein
                        organism = synthetic construct
                        note = Bivalirudin
SITE                    1
                        note = MOD_RES - D-phenylalanine
SEQUENCE: 1
FPRPGGGGNG DFEEIPEEYL                                                   20

SEQ ID NO: 2            moltype = AA  length = 18
FEATURE                 Location/Qualifiers
source                  1..18
                        mol_type = protein
                        organism = synthetic construct
                        note = [3-20] Bivalirudin
SEQUENCE: 2
RPGGGGNGDF EEIPEEYL                                                     18

SEQ ID NO: 3            moltype = AA  length = 20
FEATURE                 Location/Qualifiers
source                  1..20
                        mol_type = protein
                        organism = synthetic construct
                        note = Asp-9 Bivalirudin
SITE                    1
                        note = MOD_RES - D-phenylalanine
SEQUENCE: 3
FPRPGGGGDG DFEEIPEEYL                                                   20

SEQ ID NO: 4            moltype = AA  length = 11
```

```
FEATURE           Location/Qualifiers
source            1..11
                  mol_type = protein
                  organism = synthetic construct
                  note = [1-11] Bivalirudin
SITE              1
                  note = MOD_RES - D-phenylalanine
SEQUENCE: 4
FPRPGGGGNG D                                                              11

SEQ ID NO: 5      moltype = AA  length = 9
FEATURE           Location/Qualifiers
source            1..9
                  mol_type = protein
                  organism = synthetic construct
                  note = [12-20] Bivalirudin
SEQUENCE: 5
FEEIPEEYL                                                                  9

SEQ ID NO: 6      moltype = AA  length = 16
FEATURE           Location/Qualifiers
source            1..16
                  mol_type = protein
                  organism = synthetic construct
                  note = [5-20] Bivalirudin
SEQUENCE: 6
GGGGNGDFEE IPEEYL                                                         16
```

READY-TO-USE BIVALIRUDIN COMPOSITIONS

This application is a continuation of U.S. patent application Ser. No. 16/417,362, filed May 20, 2019, which is incorporated by reference in its entirety.

REFERENCE TO A SEQUENCE LISTING SUBMITTED AS AN XML FILE VIA PATENT CENTER

The official copy of the sequence listing is submitted electronically via Patent Center as an XML formatted sequence listing with a file named 165527-21521_SL.xml, created on Feb. 27, 2023, and having a size of 8,457 bytes, and is filed concurrently with the specification. The sequence listing contained in this XML formatted document is part of the specification and is herein incorporated by reference in its entirety.

FIELD OF THE INVENTION

The present disclosure is generally directed to storage stable, ready-to-use compositions comprising bivalirudin 3.0, wherein the compositions exhibit a pH in the range of about 3.0 to less than 4.0, or a pH in the range of from 5.0 to about 5.7. These compositions have shelf lives of at least 6, at least 9 months, or at least 12 months, when stored at 5° C. In particular embodiments, these storage-stable, ready-to-use bivalirudin compositions also include tonicity-adjusting agents, stabilizers, and/or buffering agents.

BACKGROUND

Bivalirudin is a member of the class of direct thrombin inhibitors, which have anticoagulant activity, and can thus prevent blood clotting. Direct thrombin inhibitors disrupt the activity of both circulating and clot-bound thrombin, a serine protease acting in the coagulation cascade that initiates blood clotting when fibrinogen is converted into fibrin. Bivalirudin specifically binds to thrombin's catalytic site and anion-binding exosite. Bivalirudin has a rapid onset of action, a short half-life, and is regarded as having a predictable antithrombic response. Bivalirudin overcomes many of the risks associated with indirect thrombin inhibitors, for example, heparin.

Bivalirudin has been formulated into a lyophilized drug product, e.g., ANGIOMAX® (bivalirudin) for injection. This dosage form must be reconstituted before administration, e.g., by injection such as parenteral injection. This generally requires a number of steps, including dissolution (or reconstitution) of the lyophilized drug product in a suitable liquid for injection, such as Water for Injection, 0.9% Sodium Chloride Injection, or other fluids known in the art for this purpose to yield a concentrated solution. Complete dissolution into the liquid typically requires physical manipulation, e.g., swirling or shaking, and can be time consuming. Careful dilution of the reconstituted (concentrated) solution must then be performed with the correct volume of suitable diluent, such as 0.9% Sodium Chloride Injection or 5% Dextrose Injection, to ensure the correct concentration for administration. Incomplete dissolution during the reconstitution step and/or incorrect dilution during the subsequent dilution step can lead to improper dosing, a significant component of medical error. The use of an incorrect reconstitution fluid and/or diluent can also lead to dosing errors. Such lyophilized dosage forms have been claimed in, for example, U.S. Pat. Nos. 7,582,727 and 7,598,343.

A further limitation of lyophilized drug products which must be reconstituted with a suitable liquid for injection is the relatively short shelf-life which is associated with such preparations after reconstitution and/or dilution. These reconstituted drug products are often only labelled as usable for only a few hours after reconstitution and/or dilution. For example, reconstituted ANGIOMAX® solutions are only stable for up to 24 hours at 2-8° C. and diluted ANGIOMAX® solutions are stable at 2-8° C. or room temperature for up to 24 hours.

Liquid ready-to-use bivalirudin formulations having pH of 4 to less than 5 are described and claimed in U.S. Pat. Nos. 7,713,928 and 7,803,762 (also published as U.S. Patent Publication Serial No. 2011/0046063). The most preferred pH of these formulations is 4.2-4.5, which is lower than physiological pH and thus they may not be suitable for direct infusion. These formulations are reported to show extensive degradation (37.7%, 51.1%) between pH 3 and 4 and complete degradation of the composition at pH 5 and 6 after storage for one month at 25° C.

There is thus a need for further ready-to-use injectable bivalirudin compositions having an appreciable shelf-life, e.g., suitable for storage at 5° C. for at least 6 months, or at least 9 months, or at least 12 months and with pH closer to the physiological pH range.

SUMMARY

In one aspect, the embodiments provided herein describe a ready-to-use liquid formulation of bivalirudin (label concentration of 5 mg/mL) with at least 6-, at least 9- or at least 12-month shelf life at refrigerated conditions (5±3° C., i.e., 2-8° C.). These liquid ready-to-use formulations have pH of about 3.0 to less than 4.0, or of about 3.25 to about 3.75, or alternatively, these formulations have pH of 5.0 to about 5.7; each type of formulation has a substantially similar shelf life. Additionally, these ready-to-use liquid bivalirudin compositions may be packaged as commercial off-the-shelf products, for example, are not lyophilized, have not been lyophilized as a step in their preparation (outside circumstances in which the active pharmaceutical ingredient may be supplied as a lyophilized material), and have not been reconstituted to a liquid form.

The formulations also have reduced levels of impurities upon storage, compared to previously disclosed formulations. The impurity levels at a particular time point are determined by high performance liquid chromatography ("HPLC") at a wavelength of 215 nm and compared to an initial time point, for example, the time of manufacture of the formulation, throughout this disclosure. For example, in the formulations described herein having pH in a range of about 3.0 to less than 4.0, or about 3.25 to about 3.75, or in a range of 3.3 to about 3.7, or in a range of about 3.4 to about 3.6, the amounts of total impurities as compared to an initial time point as determined by high performance liquid chromatography ("HPLC") at a wavelength of 215 nm, remain well under about 15% after storage at 25° C. for 1 month. Similarly, in the formulations described herein having pH in a range of 5.0 to about 5.7, or in a range of from about 5.1 to about 5.4, or in a range of from about 5.2 to about 5.3, the amounts of total impurities as compared to an initial time point are also well under about 15% after storage at 25° C. for 1 month, under about 10%, and under about 7.5%, and under after storage at 5° C. for 12 months. Also, in the formulations described herein, the amount of total impurities as compared to an initial time remains well under about 15%, under about 12%, under about 10% and under about 5% after storage at 5° C. for 12 months, for the formulations having pH having pH in a range of about 3.0 to less than 4.0, or about 3.25 to about 3.75, or in a range of about 3.3 to about 3.7, or in a range of about 3.4 to about 3.6, or in a range of 5.0 to about 5.7, or in a range of from about 5.1 to about 5.4, or in a range of from about 5.2 to about 5.3.

Similarly, in the formulations described herein having pH in a range of about 3.0 to less than 4.0, or of about 3.25 to about 3.75, or in a range of about 3.3 to about 3.7, or in a range of about 3.4 to about 3.6, or having pH in a range of 5.0 to about 5.7, or in a range of from about 5.1 to about 5.4, or in a range of from about 5.2 to about 5.3, the amounts of the [9-10]-cycloimido-bivalirudin or the [11-12]-cycloimido-bivalirudin impurities as compared to an initial timepoint, as determined by high performance liquid chromatography ("HPLC") at a wavelength of 215 nm, is kept well below 5% after storage at 25° C. for 1 month (see Claim 6 and Claim 7 of U.S. Pat. No. 7,713,928). For the formulations described herein, having pH in a range of about 3.0 to less than 4.0, or of about 3.25 to about 3.75, or in a range of about 3.3 to about 3.7, or in a range of about 3.4 to about 3.6, or having pH in a range of 5.0 to about 5.7, or in a range of from about 5.1 to about 5.4, or in a range of from about 5.2 to about 5.3, the amounts of the [9-10]-cycloimido-bivalirudin or the [11-12]-cycloimido-bivalirudin impurities as compared to an initial time point remain well below about 1.5%, under about 1.0%, under about 0.4%, under about 0.3%, and under about 0.25% after storage at 25° C. for 1 month or at 5° C. for about 12 months.

Also, in the formulations described herein, the amount of [3-20]-bivalirudin impurity as compared to an initial time point, as determined by high performance liquid chromatography ("HPLC") at a wavelength of 215 nm, remains well under about 1.5%, under about 1.0%, under about 0.6% and under about 0.5% after storage at 5° C. for 12 months, for the samples having pH in a range of about 3.0 to less than 4.0, or from about 3.25 to about 3.75, or in a range of 3.3 to 3.7, or in a range of 3.4 to 3.6. Also, in the formulations described herein, the amount of [3-20]-bivalirudin impurity as compared to an initial time point remains well under about 1.5% or under about 1.0% after storage at 5° C. for 12 months, for the samples having pH in a range from 5.0 to about 5.7, or in a range of from about 5.1 to about 5.4, or in a range of from about 5.2 to about 5.3.

The ready-to-use bivalirudin compositions disclosed herein are considered storage stable.

The formulations may contain tonicity-adjusting and/or stabilizing agents, which can be selected from the group consisting of, for example, salts such as potassium chloride, sodium chloride, for example 0.9% NaCl; saccharides (e.g., monosaccharides, disaccharides, polysaccharides) such as, lactose, trehalose, raffinose, dextrose, maltose, galactose, sucrose, and polysucrose, sugar alcohols such as mannitol, for example, 5% D-mannitol, sorbitol, or xylitol; polymers such as polygalacturonic acid, polyethylene glycol (PEG), polyvinylpyrrolidine (PVP), for example, PEG 300, PEG 400, PEG 3350, PEG 6000, PEG 8000 and the like, for example 10% w/v PEG 400; amino acids such as lysine, arginine, glycine, methionine, and other amino acids; and other materials such as dextran, cyclodextrins (for example, hydroxypropyl-γ-cyclodextrin, Ficoll, galacturonic acid, and other similar excipients. These formulations may also contain further excipients, such as buffering agents, pH-adjusting agents, preservatives, osmolality-adjusting agents, and solubilizing agents.

In some embodiments, an injectable ready-to-use bivalirudin composition of the invention comprises:
  a. bivalirudin (SEQ ID NO: 1), or salts thereof,
  b. one or more pharmaceutically acceptable agent(s) selected from the group consisting of buffering agents, tonicity-adjusting agents, stabilizing agents, antioxidants, and pH adjusting agents, and
  c. a pH ranging from (i) 5.0 to about 5.7 or (ii) about 3.0 to less than 4.0, wherein the percentage of total impurities increases by no more than about 9% from the time of manufacture up to 12 months of storage at 5° C. or up to 1 month of storage at 25° C. as determined by high performance liquid chromatography at a wavelength of 215 nm.

In some embodiments, the one or more pharmaceutically acceptable agent(s) comprises a tonicity-adjusting agent and/or a stabilizing agent. In some embodiments, the tonicity-adjusting agent and/or the stabilizing agent comprises (i) an inorganic chloride, (ii) a saccharide, sugar alcohol or an amino sugar, (iii) an amino acid, (iv) an organic solvent, or (vi) any combination of (i)-(iv). In some embodiments, the tonicity-adjusting and/or the stabilizing agent comprises polyethylene glycol (PEG), mannitol, sucrose, glycerol, ethanol, sorbitol, glycine, proline, or any combination thereof.

In some embodiments, the pH of a composition of the invention ranges from 5.0 or more to about 5.7. In some embodiments, the one or more pharmaceutically acceptable agent(s) comprises a buffering agent having at least one pKa from about 4.0 to about 6.7. In some embodiments, the buffering agent is selected from the group consisting of acetate, oxalate, acrylate, ascorbate, benzoate, caprate, caproate, caprylate, cinnamate, fumarate, maleate, phosphate, orthophosphate, laurate, palmitate, propionate, adipate, cacodylate, malonate, propionate, hydroxypropionate, fumarate, phthalate, maleate, 3- or 4-hydroxybutanoate, butenoate, crotonate, methylmalonate, succinate, malate, tartrate, citrate, 2-(N-morpholino)ethanesulfonic acid ("MES"), salts thereof, and any combination thereof. In some embodiments, the percentage of Asp 9-bivalirudin increases by no more than about 2% from the time of manufacture up to 12 months of storage at 5° C. or up to 1 month of storage at 25° C. as determined by high performance liquid chromatography at a wavelength of 215 nm; the percentage of [3-20]-bivalirudin increases by no more than about 2% from the time of manufacture up to 12 months of storage at 5° C. or up to 1 month of storage at 25° C. as determined by high performance liquid chromatography at a wavelength of 215 nm; the percentage of [9-10]-cycloimido-bivalirudin increases by no more than about 2% from the time of manufacture up to 12 months of storage at 5° C. or up to 1 month of storage at 25° C. as determined by high performance liquid chromatography at a wavelength of 215 nm, the percentage of [11-12]-cycloimido-bivalirudin increases by no more than about 2% from the time of manufacture up to 12 months of storage at 5° C. or up to 1 month of storage at 25° C. as determined by high performance liquid chromatography at a wavelength of 215 nm, and/or the percentage of total impurities increases by no more than about 8% from the time of manufacture up to 12 months of storage at 5° C. or up to 1 month of storage at 25° C. as determined by high performance liquid chromatography at a wavelength of 215 nm. In some embodiments, the one or more pharmaceutically acceptable agent(s) comprises (i) sodium acetate and (ii) a tonicity-adjusting agent and/or a stabilizing agent selected from the group consisting of polyethylene glycol (PEG), mannitol, sucrose, glycerol, ethanol, sorbitol, glycine, proline, and any combination thereof.

In some embodiments, a composition of the invention comprises
about 1 to about 10 mg/mL bivalirudin,
about 1 mM to about 50 mM sodium acetate,
about 5% to about 12.5% PEG by weight, and
a pH of about 5.25.

In some embodiments, a composition of the invention comprises
about 2.5 to about 7.5 mg/mL bivalirudin,
about 5 mM to about 30 mM sodium acetate,
about 7.5 to about 10% PEG by weight, and
a pH of about 5.25.

In some embodiments, a composition of the invention comprises
about 5 mg/mL bivalirudin,
about 6 mM sodium acetate,
about 10% PEG 400 by weight, and
a pH of about 5.25.

In some embodiments, a composition of the invention comprises a pH ranging from about 3.0 to less than 4.0.

In some embodiments, a composition of the invention comprises
about 1 to about 10 mg/mL bivalirudin,
about 1 mM to about 300 mM glycine,
about 5% to 12.5% PEG by weight, and
a pH of about 3.50.

In some embodiments, a composition of the invention comprises
about 1 to about 10 mg/mL bivalirudin,
about 5 mM to about 50 mM glycine,
about 7.5% to 10% PEG by weight, and
a pH of about 3.50. In some embodiments, a composition of the invention comprises
about 5 mg/mL bivalirudin,
about 10 mM glycine,
about 10% PEG by weight, and
a pH of about 3.50.

In some embodiments, the percentage of Asp 9-bivalirudin increases by no more than about 0.6% from the time of manufacture up to 12 months of storage at 5° C. or up to 1 month of storage at 25° C. as determined by high performance liquid chromatography at a wavelength of 215 nm, the percentage of [12-20]-bivalirudin increases by no more than about 4% from the time of manufacture up to 12 months of storage at 5° C. or up to 1 month of storage at 25° C. as determined by high performance liquid chromatography at a wavelength of 215 nm, the percentage of [3-20]-bivalirudin increased by no more than about 1% from the time of manufacture up to 12 months of storage at 5° C. or up to 1 month of storage at 25° C. as determined by high performance liquid chromatography at a wavelength of 215 nm, the percentage of [11-12]-cycloimido-bivalirudin increases by no more than about 2.5% from the time of manufacture up to 12 months of storage at 5° C. or up to 1 month of storage at 25° C. as determined by high performance liquid chromatography at a wavelength of 215 nm, the percentage of [9-10]-cycloimido-bivalirudin increases by no more than about 0.5% from the time of manufacture up to 12 months of storage at 5° C. or up to 1 month of storage at 25° C. as determined by high performance liquid chromatography at a wavelength of 215 nm, and/or the percentage of total impurities increases by no more than about 7.5% from the time of manufacture up to 12 months of storage at 5° C. or up to 1 month of storage at 25° C. as determined by high performance liquid chromatography at a wavelength of 215 nm. In some embodiments, a pharmaceutical composition of the invention comprises a sterile, storage stable ready-to-use liquid composition that comprises a therapeutically effective amount of bivalirudin, a pharmaceutically acceptable carrier, and less than about 19% total bivalirudin impurities, and a sterile ready-to-use container pre-packaged with the storage stable ready-to-use liquid composition.

In some embodiments, a composition is a commercial off-the-shelf pharmaceutical product. In some embodiments, the liquid composition comprises
about 5 mg/mL bivalirudin,
about 10 mM glycine or about 6 mM sodium acetate,
About 10% PEG 400 by weight, and
a pH of about 3.5 or 5.25.

In a further aspect, the embodiments provided herein describe methods of using the ready-to-use liquid formulations of bivalirudin described herein.

In some embodiments, a method for inhibiting blood clots in a mammal is provided comprising administering a therapeutically effective amount of a composition, e.g., pharmaceutical composition as described herein the mammal in need thereof, wherein the administration does not involve reconstitution of a lyophilized bivalirudin composition. In some embodiments, the compositions comprise less than about 19% total impurities.

In another further aspect, the embodiments provided herein describe methods of preparing the ready-to-use liquid formulations of bivalirudin described herein.

DETAILED DESCRIPTION

Bivalirudin is a synthetically-produced, 20-amino acid peptide with the following amino acid sequence, and a molecular weight of 2180 daltons in its free base form:
D-Phe-Pro-Arg-Pro-Gly-Gly-Gly-Gly-Asn-Gly-Asp-Phe-Glu-Glu-Ile-Pro-Glu-Glu-Tyr-Leu (SEQ ID NO: 1)

A commonly used salt is the trifluoroacetate salt hydrate, and as used herein, the term "bivalirudin" refers to the peptide comprising SEQ ID NO: 1 and salts thereof The term "therapeutically effective amount" as used herein is interchangeable with "effective amount" for purposes herein, and is determined by such considerations as are known in the art. The amount must be effective to achieve a desired drug-mediated effect in the treated subjects suffering from the disease thereof. A "therapeutically effective amount" also includes, but is not limited to, consideration of appropriate measures selected by those skilled in the art, for example, improved survival rate, more rapid recovery, or amelioration, improvement or elimination of symptoms. The term "about" in relation to pH units means plus or minus 0.2 pH units.

The term "storage stable" as used herein means a composition that is stable in storage as ready-to-use (e.g., liquid) compositions that are stable in storage. Such storage stable compositions refer to those in which the composition maintains bivalirudin in its active form, and/or has a limited formation of impurities after manufacture, and/or maintains the pH within a selected range (e.g., about 3.0 to less than 4.0, or about 3.25 to about 3.75, or about 3.3 to about 3.7, or about 3.4 to about 3.6, or 5.0 to about 5.7, or about 5.1 to about 5.4 or 5.2 to about 5.3) upon storage at a selected temperature for a selected time period.

Peptides containing glutamine and asparagine residues are generally difficult to stabilize in liquid drug formulations, due to the multitude of degradative pathways to which such peptides are susceptible. Glutamine and especially asparagine residues can undergo deamidation, which are catalyzed at neutral and alkaline pH through the formation of a succinimide intermediate. This reaction can also occur at acidic pH through direct hydrolysis of an asparagine residue. It is thus difficult to avoid this degradation by pH adjustment, and drug products containing peptides with these specific amino acids often have been prepared as lyophilizates in an effort to avoid such issues by minimizing contact with aqueous media.

In one aspect, the embodiments provided herein describe a ready-to-use liquid formulation of bivalirudin (e.g., 5 mg/mL) with at least 6 months, at least 9 or at least 12 months shelf life at refrigerated conditions (5±3° C., i.e., 2-8° C.). These compositions are storage stable. A "storage stable" composition refers to a composition that is stable in storage and refers to ready-to-use or ready-to-dilute aqueous (e.g., liquid) compositions that are stable in storage. Such storage stable compositions refer to those in which the composition maintains bivalirudin in its active form and/or has a limited amount of impurities and/or maintains the pH within the desired range upon storage at a selected temperature for a selected time duration after manufacture of the formulation. Storage stability also implies lower impurity levels upon such storage, as compared to previously disclosed liquid ready-to-use bivalirudin compositions.

For example, a composition is considered storage stable under certain conditions so long as the composition retains at least 90% of its active bivalirudin and/or increases in total impurities remain less than about 10%, 7% or 5% as compared to an initial time point, as determined by high performance liquid chromatography ("HPLC") at a wavelength of 215 nm, for compositions with pH values between 5.0 and about 5.7, or less than about 10% or 7.5% for compositions with pH values of about 3.0 to less than 4.0, or from about 3.25 to about 3.75.

In some embodiments, a composition is considered storage stable so long as the composition does not exhibit an increase of more than about 0.6%, or more than about 0.5%, or more than about 0.25% Asp 9-bivalirudin (SEQ ID NO:3) as compared to an initial time point, as determined by high performance liquid chromatography ("HPLC") at a wavelength of 215 nm for compositions having pH in the range of about 3.0 to less than 4.0, or about 3.25 to about 3.75. In some embodiments, a composition is considered storage stable so long as the composition does not exhibit an increase of more than about 1.5% or more than about 1.0%, or more than about 0.75% or more than about 0.6% Asp 9-bivalirudin as compared to an initial time point, as determined by high performance liquid chromatography ("HPLC") at a wavelength of 215 nm for compositions having pH in the range of 5.0 to about 5.7.

In some embodiments, a composition is considered stable so long as the composition does not exhibit increases more than about 1.0% or more than about 0.5% [3-20]-bivalirudin (SEQ ID NO:2) as compared to an initial time point, as determined by high performance liquid chromatography ("HPLC") at a wavelength of 215 nm for compositions having pH in the range of about 3.0 to less than 4.0, or about 3.25 to about 3.75. In some embodiments, a composition is considered stable so long as the composition does not exhibit increases more than about 2.0%, or more than about 1.8%, or more than 1.5% [3-20]-bivalirudin as compared to an initial time point, as determined by high performance liquid chromatography ("HPLC") at a wavelength of 215 nm for compositions having pH in the range of 5.0 to about 5.7.

In some embodiments, a composition is considered stable so long as no individual unknown impurity makes up more than 2% or more than 1% of the composition. In some embodiments, a composition is considered stable so long as the initially adjusted pH remains within ±1.0 pH unit, or within ±0.75 pH units, or within ±0.5 pH units, or within ±0.25 pH units. "Shelf-life" refers to the amount of time a composition remains stable under certain conditions.

Influence of pH and Stabilizers

The predominant degradation mechanisms of peptides (such as deamidation) are known to be pH dependent. In addition to the pH, the role of various stabilizers was also investigated ranging from buffers, saccharides (e.g., sucrose, mannitol, sorbitol), amino acids (e.g., glycine, proline), and organic co-solvents (e.g., polyethylene glycol, ethanol, glycerol). Different buffer species (e.g., acetate, citrate, citrate-phosphate) and levels of buffers were investigated to understand if there was any buffer-induced catalysis.

Formulations have been identified, for example, ready-to-use bivalirudin formulations having a pH of about 3.0 to less than 4.0, or from about 3.25 to about 3.75 acceptable for pharmaceutical use, and ready-to-use bivalirudin formulations having a pH from 5.0 to around 5.7 acceptable for pharmaceutical use. In addition, various buffers and concentrations of buffers were also investigated, as disclosed below.

Bivalirudin

Bivalirudin can be synthesized by methods that include, but are not limited to, solid-phase peptide synthesis, solution-phase peptide synthesis, or a combination of these techniques (e.g., U.S. Pat. No. 5,196,404, U.S. Patent Application 2007/0093423, and other references known to those of skill in the art). These citations are incorporated by reference in their entireties.

The bivalirudin of the ready-to-use compositions described herein may be the peptide encoded by SEQ ID NO: 1, or salts thereof. In particular embodiments, the trifluoroacetate salt may be employed. The bivalirudin concentrations disclosed herein is the actual bivalirudin (free base) content. Bivalirudin may be present in amounts ranging from about 0.01 mg/mL, to about 100 mg/mL, or from about 0.05 to about 50 mg/mL, or between about 0.1 mg/mL and about 25 mg/m or between about 1.0 mg/mL and about 10 mg/mL, or between about 2.5 mg/mL and about 7.5 mg/mL, such as 5.0 mg/mL.

Tonicity-Adjusting and Stabilizing Agents

Tonicity-adjusting agents, as used herein, are excipients which adjust the tonicity of the liquid ready-to-use bivalirudin compositions to a desired isotonic range. For physiologically acceptable compositions, "isotonic" can include compositions which have similar tonicities to human serum. An acceptable range would be approximately 200 to 600 mOsm/kg. Stabilizers may also be advantageously in the liquid ready-to-use bivalirudin compositions described herein. Particular materials introduced in the disclosed formulations may function as both a tonicity agent and a stabilizer. In such instances, such materials may be used at concentrations higher than needed for tonicity if their primary purpose is stabilization, or may be used at concentrations higher than needed for stabilization if their primary purpose is tonicity adjustment. Tonicity-adjusting agents and/or stabilizing agents for use in the presently disclosed compositions can include, but are not limited to, for example, pharmaceutically acceptable inorganic chlorides, e.g., potassium chloride, sodium chloride, magnesium chloride or calcium chloride, for example 0.9% NaCl; saccharides (monosaccharides, disaccharides, polysaccharids, etc.) such as, e.g., mannitol (including D-mannitol), sorbitol, lactose, trehalose, raffinose, dextrose, maltose, galactose, sucrose, and polysucrose, for example, 5% D-mannitol; polymers such as polygalacturonic acid, polyethylene glycol (PEG), polyvinylpyrrolidine (PVP), for example,PEG 300, PEG 400, PEG 3350, PEG 6000, PEG 8000 and the like, for example 10% w/v PEG 400; amino acids such as lysine, arginine, glycine, methionine, and other amino acids; and other materials such as dextran, cyclodextrins (for example, hydroxypropyl-γ-cyclodextrin, Ficoll, galacturonic acid, and other similar excipients and combinations of these agents. These agents may be present in the compositions in amounts of from about 0.25% to about 15% percent by weight of the formulation. Specific stabilizers such as proline and polyethylene glycol can also be used to reduce degradation rates.

Further stabilizing excipients which may be employed include: poly alcohols, including glycerol, propylene glycol, and others; dielectric strength modifiers, including ethanol, polyethylene glycol, propylene glycol, glycerol and others; amino acids, including for example, proline, glycine, histidine, methionine and others. Furthermore, as the formulations disclosed herein are not designed to undergo lyophilization, agents whose primary function is lyoprotection or cryoprotection are generally not employed.

Buffers

In embodiments disclosed herein, the pH of the ready-to-use bivalirudin compositions disclosed herein is in a range of about 3.0 to less than 4.0, or between about 3.25 and about 3.75, or in a range of from 3.3 to 3.7, or from 3.4 to 3.6. In other embodiments described herein, the pH of the final ready-to-use bivalirudin compositions disclosed herein is in a range of 5.0 to about 5.7, or in a range from about 5.1 to about 5.4, or from about 5.2 to about 5.3. Buffers, as used herein, are pharmaceutically acceptable reagents or compositions which can contribute to maintenance of the pH of the ready-to-use bivalirudin compositions to a desired pH range, i.e., about 3.0 to less than 4.0, or from about 3.25 to about 3.75, or from 3.3 to 3.7 or from 3.4 to 3.6, or from 5.0 to about 5.7, or from about 5.1 to about 5.4, or from 5.2 to 5.3.

As used herein, the term "buffer" means excipients having ionizable groups with pKa values around the target pH of the bivalirudin compositions, plus or minus about one pH unit. For formulations having a pH in a range of about 3.0 to less than 4.0, or between about 3.25 and about 3.75, or in a range of from 3.3 to 3.7, or from 3.4 to 3.6, a buffer should have at least one pKa of about 2.0 to about 5.0. For formulations having a pH from 5.0 to about 5.7, or from about 5.1 to about 5.4, or from 5.2 to 5.3, a buffer should have at least one pKa of about 4.0 to about 5.57.

Such buffers which may be suitable for use in the ready-to-use bivalirudin compositions disclosed herein include, but are not limited to, for example in the pKa 2.0-5.0 range: acetate, acetoacetate, adipate, alginate, ascorbate, aspartate, benzoate, acrylate, butenoate, glyoxylate, butanoate, oxobutanoate, 2-, 3- or 4-chlorobutanoate, lactobionate, succinate, α-lipoic acid, maleate, bromoacetate, chloroacetate, cyanoacetate, 2- or 3-chloropropionate, citrate, citrate-phosphate, bicarbonate, tartrate, glycylglycine, formate, fumarate, glycerate, glycine, crotonate, lactate, malate, malonate, methylmalonate, melaminate, oxaloacetate, oxalate, propionate, methylpropionate, and 3- or 4-hydroxypropionate, pyridine, piperazine, phosphate, pyrophosphate, pyruvate, phthalate, histidine, (bis(2-hydroxyethyl)-imino-tris(hydroxymethyl)-methane) ("bis-TRIS"), trimethylamine oxide, bicarbonate, and other buffers with pKa in this range, and their various salts and anhydrous or hydrated forms, or some combination of such buffers.

Such buffers which may be suitable for use in the ready-to-use bivalirudin compositions disclosed herein include, but are not limited to, for example in the pKa 4-6.7 range: acetate, oxalate, acrylate, ascorbate, benzoate, caprate, caproate, caprylate, cinnamate, fumarate, maleate, phosphate, orthophosphate, laurate, palmitate, propionate, adipate, cacodylate, malonate, propionate, hydroxypropionate, fumarate, phthalate, maleate, 3- or 4-hydroxybutanoate, butenoate, crotonate, methylmalonate, succinate, malate, tartrate, citrate, 2-(N-morpholino)ethanesulfonic acid ("MES"), and other buffers with pKa in this range, and their various salts and anhydrous or hydrated form or some combination of such buffers. These buffers may be present in the compositions in amounts of about 1 mM to about 500 mM, or about 5 mM to about 300 mM. An acetate buffer such as sodium acetate (in its anhydrous or hydrated form, e.g., sodium acetate trihydrate) may be used for the higher pH (5.0 to about 5.7) formulations disclosed herein.

pH-Adjusting Agents

The pH of particular embodiments of the final ready-to-use bivalirudin compositions disclosed herein is in a range of about 3.0 to less than 4.0, or between about 3.25 and about 3.75, or from 3.3 to 3.7 or from 3.4 to 3.6. The pH of other particular embodiments of the final ready-to-use bivalirudin compositions disclosed herein is in a range of 5.0 to about 5.7, or from about 5.1 to about 5.4, or from 5.2 to 5.3. The ready-to-use bivalirudin compositions described herein may employ pH-adjusting agents to adjust the pH of the compositions described herein to a target range or value. For example, during the preparation of a ready-to-use bivalirudin composition disclosed herein, bivalirudin may be added to a buffering agent, with an associated change in pH of the buffer solution. pH-adjusting agents could be added to achieve a desired pH. e.g., about 3.0 to less than 4.0, or from about 3.25 to about 3.75, or from 3.3 to 3.7, or from 3.4 to 3.6, or from greater than or equal to 5.0 to about 5.7, or from about 5.1 to about 5.4, or from 5.2 to 5.3. The pH-adjusting agents can include pharmaceutically acceptable acids, bases or buffering agents. The pharmaceutically acceptable acids could include, but are not limited to, for example, one or more inorganic mineral acids such as hydrochloric, sulfuric, phosphoric, nitric and the like; or one or more organic acids, e.g., acetic, succinic, tartaric ascorbic, citric, glutamic, benzoic, methanesulphonic, ethanesulphonic, trifluoroacetic and the like.

The pharmaceutically acceptable bases may be one or more inorganic or organic bases (e.g., sodium acetate or the like), including but not limited to, for example, alkaline carbonate (e.g., calcium carbonate, sodium carbonate or the like), alkaline bicarbonate (e.g., sodium bicarbonate or the like), alkaline earth metal carbonate, alkaline hydroxide (e.g., lithium hydroxide, potassium hydroxide, cesium hydroxide, sodium hydroxide or the like), alkaline earth metal hydroxide or amine. Salts of pH-adjusting agents may also be used. In particular formulations having pH in the range of about 3.0 to less than 4.0, sodium hydroxide and/or hydrochloric acid solutions were used to adjust the pH to the desired value, as needed. In other particular formulations, for example those having pH in the range of 5.0 to about 5.7, glacial acetic acid and/or sodium hydroxide solution were used to adjust the pH to the desired value, as needed.

Methods of Making Ready-to-Use Bivalirudin Compositions

The ready-to-use liquid bivalirudin compositions can be prepared by methods described herein. The methods comprise mixing one or more tonicity-adjusting and/or stabilizing agents and one or more buffers with bivalirudin to form the ready-to-use bivalirudin compositions. Optionally, the methods can also comprise providing pH-adjusting agents to such mixtures, to adjust the pH of the ready-to-use bivalirudin compositions if the pH is not within a desired pH range, e.g., about 3.0 to less than 4.0, or from about 3.25 to about 3.75, or from 3.3 to 3.7, or from 3.4 to 3.6, or from greater than or equal to 5.0 to about 5.7, or from about 5.1 to about 5.4, or from 5.2 to 5.3.

The one or more tonicity-adjusting and/or stabilizing agents can first be dissolved in aqueous media prior to mixing with bivalirudin. The tonicity-adjusting and/or stabilizing agents can comprise any of the materials discussed herein or known to the person of ordinary skill in the art. The one or more tonicity-adjusting and/or stabilizing agents and/or buffer may be dissolved in aqueous media, optionally containing one or more buffers, by methods known in the art. For example, the tonicity-adjusting and/or stabilizing agents may be dissolved by adding each agent, and optionally one or more buffers, to aqueous media (optionally containing one or more buffers), by adding the agents, and optionally one or more buffers, to each other and then mixing them with aqueous media (optionally containing one or more buffers), by mixing the one or more tonicity-adjusting and/or stabilizing agents, and optionally one or more buffers, and aqueous media (optionally containing one or more buffers) in a common vessel, or a combination thereof The one or more tonicity-adjusting and/or stabilizing agents, and optionally one or more buffers, can be added simultaneously, individually in a particular order, individually in no particular order, all at once or in a particular sequence, including partial additions of portions of either or both types of components, followed by continued additions of either or both types of components until the desired amounts of components are added, or some combination thereof. Reasons for adding tonicity-adjusting and/or stabilizing agents, and optionally one or more buffers, in a given order may include, but are not limited to, preventing some reaction between tonicity-adjusting and/or stabilizing agents and/or one or more buffers, which might be mixed together directly, stimulating a reaction that may occur when tonicity-adjusting and/or stabilizing agents and/or one or more buffers are mixed directly together, maintaining a given pH, maintaining a given tonicity, and ease of handing.

The aqueous media can be introduced to a suitable vessel at an elevated temperature, for example from about 35° C. to about 90° C., or from about 50° C. to about 85° C., or from about 60° C. to about 85° C., for example, about 80° C. The aqueous media can then optionally be brought to and held at a temperature, for example, of about 2° C. to about 35° C., or from about 10° C. to about 35° C., or from about 15° C. to about 30° C., or from about 20° C. to about 25° C., for the mixing processes described herein.

The one or more tonicity-adjusting and/or stabilizing agents and/or the one or more buffers can be dissolved or made miscible in aqueous media, optionally containing one or more buffers, using mixing technologies and devices known to those of skill in the art. Examples of mixing devices may include, but are not limited to, paddle mixers, magnetic stirring devices, shakers, re-circulating pumps, homogenizers, and combinations thereof. The mixing speeds of any of the mixing steps can be selected from, for example, not less than 50 rpm, or not less than 100 rpm, or not less than 250 rpm, or for example, not less than 200 rpm, for minimum times of at least 5 minutes, at least 10 minutes at least 15 minutes, at least 30 minutes, or at least 45 minutes. The dissolution of one or more tonicity-adjusting and/or stabilizing agents and/or the one or more buffers may occur under controlled conditions, for example, under temperature control or atmospheric control (e.g., under nitrogen or with a particular humidity) through means known in the art.

Thereafter, bivalirudin (in solution or as a solid, for example, a lyophilized material) may be mixed with the dissolved tonicity-adjusting and/or stabilizing agents, optionally containing one or more buffers, again using methods known in the art. Bivalirudin can be added to the dissolved tonicity-adjusting and/or stabilizing agents and/or the one or more optional buffers rapidly or slowly, all at once or in portions, in a constant rate or at variable rates or a combination of all these techniques. The bivalirudin can be combined with the one or more tonicity-adjusting and/or stabilizing agents and/or the one or more optional buffers using mixing technologies and devices known to those of skill in the art. Examples of mixing devices may include, but are not limited to, paddle mixers, magnetic stirring devices, shakers, re-circulating pumps, homogenizers, and combinations thereof. Mixing techniques can include those classified as "efficient," for example those described in U.S. Pat. Nos. 7,582,727, 7,598,343, and others. The dissolution of bivalirudin with the one or more tonicity-adjusting and/or stabilizing agents and/or the one or more optional buffers may occur under controlled conditions, for example, under temperature control or atmospheric control (e.g., under nitrogen and/or with a particular humidity) through means known in the art.

The bivalirudin could already be dissolved in aqueous medium (optionally containing one or more buffers) when it is mixed with the tonicity-adjusting and/or stabilizing agents and/or one or more optional buffers. On the other hand, the bivalirudin could be mixed in its solid form (for example, a lyophilized form) with the dissolved tonicity-adjusting and/or stabilizing agents and/or one or more optional buffers. Alternatively, the bivalirudin can be mixed with one or more tonicity-adjusting and/or stabilizing agents prior to dissolution in aqueous media (optionally containing one or more buffers), simultaneously with dissolution in aqueous media (optionally containing one or more buffers), or a combination thereof. The use of a lyophilized form of bivalirudin in such formulations does not mean that the formulation itself has been lyophilized. As set forth herein, the bivalirudin formulations, but not necessarily the active pharmaceutical ingredient, are prepared without having been lyophilized at any stage.

Resulting solutions comprising the dissolved bivalirudin, tonicity-adjusting and/or stabilizing agents and optional buffers are ready-to-use bivalirudin compositions as described herein. In particular embodiments of the disclosure herein, a desired pH range for some embodiments of the liquid ready-to-use bivalirudin compositions is about 3.0 to less than 4.0, or about 3.25 to about 3.75, or 3.3 to 3.7, or 3.4 to 3.6, and another desired pH range for other embodiments of the liquid ready-to-use bivalirudin compositions is greater than or equal to 5.0 to about 5.7, or about 5.1 to about 5.4, or 5.2 to 5.3. If the pH of the ready-to-use bivalirudin compositions is not in the respective desired range after performing the methods described above, one or more pH-adjusting agents can be added to the compositions to provide a pH in the desired range. Further, if a specific concentration of bivalirudin is desired in the ready-to-use bivalirudin compositions, the concentration can be adjusted, for example, by addition of aqueous media to the compositions. Some liquid ready-to-use bivalirudin concentrations of the formulations described herein can be 125 mg/25 mL, or 250 mg/50 mL, for example.

After the ready-to-use bivalirudin compositions are prepared, they can be sterilized as desired, using any suitable techniques known in the art. For example, the aqueous composition can be made to undergo aseptic filtration using, for example, a suitable filter such as a 0.2 μm membrane filter. Sterilization may also or alternatively involve a freeze-thaw cycle to eliminate any residual vegetative bacteria.

The ready-to-use liquid bivalirudin compositions can be placed in containers having a sterile access port for piercing by hypodermic injection needles, for example, an intravenous solution bag, bottle, stoppered vial, ampoule, pre-filled sterile syringe, together with instructions for administration. Also, for example, the formulations can be filled into so-called "piggy back" vials that can be pierced directly with the universal port of an IV administration set and hung to administer with no preparation steps.

Methods of Using Ready-to-Use Bivalirudin Compositions

The ready-to-use liquid bivalirudin compositions can be useful in methods of treating a patient in need of administration of such bivalirudin compositions. The methods comprise administration of a ready-to-use bivalirudin composition comprising bivalirudin and one or more tonicity-adjusting and/or stabilizing agents and any optional buffer. The ready-to-use bivalirudin can be any ready-to-use bivalirudin composition described herein.

The ready-to-use bivalirudin composition can be an injectable dosage form, and they can be delivered to a patient parenterally. Methods of administering ready-to-use bivalirudin compositions parenterally are known in the art. For example, an aqueous composition can be delivered intravenously.

The aqueous composition may be an intravenous bolus dose of between about 0.25 mg/kg and about 1.5 mg/kg, or between about 0.5 mg/kg to about 1 mg/kg, or about 0.75 mg/kg. This may be followed by an infusion of between about 1.25 mg/kg/h and about 2.25 mg/kg/h, or about 1.75 mg/kg/h for the duration of the procedure or treatment protocol. Five minutes after the bolus dose is administered, an additional bolus of between about 0.1 mg/kg and about 1 mg/kg, or about 0.3 mg/kg, may be given if needed.

The ready-to-use bivalirudin compositions disclosed herein may be indicated for use as an anticoagulant, for example, for patients with unstable angina, for example, those patients with unstable angina undergoing percutaneous transluminal coronary angioplasty (PTCA). Such compositions may also be indicated for patients that may have, or be at risk of having, heparin-induced thrombocytopenia (HIT) and/or heparin-induced thrombocytopenia and thrombosis syndrome (HITTS) undergoing percutaneous coronary intervention (PCI). Such compositions may also be indicated for patients undergoing PCI with provisional use of glycoprotein IIb/IIIa (GPI). The ready-to-use bivalirudin compositions disclosed herein may also be used for the prevention and/or treatment of venous thromboembolic diseases.

The ready-to-use bivalirudin compositions described herein can be administered with other drug products such as glycoprotein IIb/IIIa inhibitor (see, e.g., Allie et al., Vasc. Dis. Manag., 3 (2006) 368-75). Alternatively, the compositions disclosed herein may be used in combination with blood thinners, including but not limited to, for example, coumadin, warfarin or aspirin.

EXAMPLES

The examples disclosed herein illustrate some of the embodiments of the present disclosure in greater detail, and do not limit the scope of any claims made herein.

Example 1—Bivalirudin Assay of the Listed Drug (Angiomax®)

To understand the impact of the drug preparation procedure on the actual concentration of bivalirudin in diluted Angiomax solutions, three lots of the listed drug, Angiomax® were each prepared by each of the following two methods
A. following the exact procedure specified in the package insert; namely, withdrawing 5 mL of the diluent (0.9% Sodium Chloride Injection) from a 50 mL IV bag of the diluent, before transferring the entire contents of the reconstituted vial to the bag; or
B. adding the contents of the reconstituted vial to accurately measured 45 mL of diluent (0.9% Sodium Chloride Injection), In both cases, each vial of Angiomax® was first reconstituted in 5 mL of Sterile Water for Injection as per the package insert, prior to dilution as described above. The data are summarized in Table 1.

TABLE 1

Assay of Angiomax ® (bivalirudin) for Injection Admixture as a Function of (bivalirudin) for Injection, Assay (%)

| Preparation Method | Angiomax ® (bivalirudin) for Injection, Assay (%) (Nominal = 5 mg/mL) | | |
| --- | --- | --- | --- |
| | Lot 00103 | Lot 00111 | Lot 00106 |
| Prepared exactly as per PI | 88.6 | 92.2 | 88.0 | 89.6 |
| Prepared in exactly 45 mL of Diluent | 98.6 | 102.8 | 102.0 | 102.2 |

The results show that the bivalirudin concentrations of three representative lots, when prepared as per the Angiomax® package insert, are consistently below the nominal concentration of 5 mg/mL by about 8-12%, thus resulting in significant under-dosing of patients, resulting in acute stent thrombosis and/or adverse effects. This is believed to be a direct result of the overfill volume in the diluent bag because vials prepared by diluting the content of the reconstituted vial in 45 mL of diluent are consistently at the nominal concentration. The liquid ready-to-use products described and claimed herein are ready-to-use and supplied at a 5 mg/mL concentration and require no dilution or additional preparation for use in the PCI procedure.

Example 2—Stability Testing of Disclosed Bivalirudin Formulations

Exemplary compositions according to the present disclosure were tested for storage stability. Bivalirudin was used in 2.5 mg/mL or 5 mg/mL concentrations. For each exemplary composition, initial levels of the various degradants were measured, and samples were generally subjected to stability testing at 40° C./75% RH, 2-8° C., and/or 25°

C./60% RH. Table 2 lists exemplary liquid ready-to-use bivalirudin formulations, sorted by target pH

TABLE 2

Liquid Bivalirudin Formulations, Sorted by pH

| Form. | Target pH | Buffer | Stabilizer/Tonicity agent |
|---|---|---|---|
| A | 2.5 | 3.8 mg/mL glycine | None |
| B | 2.5 | 5.25 mg/mL citric acid monohydrate/ 2.68 mg/mL dibasic sodium phosphate | None |
| C | 3.0 | 3.8 mg/mL glycine | None |
| D | 3.0 | 5.25 mg/mL citric acid monohydrate/ 2.68 mg/mL dibasic sodium phosphate | None |
| E | 3.0 | 0.8 mg/mL glycine | 9 mg/mL NaCl |
| F | 3.0 | 14.7 mg/mL sodium citrate dihydrate | 9 mg/mL NaCl |
| G | 3.0 | 3.8 mg/mL glycine | 9 mg/mL NaCl |
| H | 3.25 | 3.8 mg/mL glycine | 98 mg/mL NaCl |
| I | 3.5 | None | 3.8 mg/mL glycine |
| J | 3.5 | 5.25 mg/mL citric acid monohydrate/ 2.68 mg/mL disbasic sodium phosphate | None |
| K | 3.5 | None | 9 mg/mL NaCl/ 3.8 mg/mL glycine |
| L | 3.5 | None | 50 mg/mL mannitol/ 3.8 mg/mL glycine |
| M | 3.5 | None | 9 mg/mL NaCl/ 3.8 mg/mL glycine |
| N | 3.5 | None | 9 mg/mL NaCl/ 0.8 mg/mL glycine |
| O | 3.5 | None | 100 mg/mL sucrose/ 3.8 mg/mL glycine |
| P | 3.5 | 14.7 mg/mL sodium citrate dihydrate | 9 mg/mL NaCl |
| Q | 3.5 | None | 6.8 mg/mL sodium acetate trihydrate/ 9 mg/mL NaCl |
| R | 3.5 | None | 150 mg/mL sorbitol/ 3.8 mg/mL glycine |
| S | 3.5 | None | 22.5 mg/mL glycine |
| T | 3.5 | None | 100 mg/mL PEG 400/ 3.8 mg/mL glycine |
| U | 3.5 | None | 150 mg/mL sorbitol; 100 mg/mL PEG 400/ 3.8 mg/mL glycine |
| V | 3.5 | None | 28.5 mg/mL L-proline/ 3.8 mg/mL glycine |
| W | 3.5 | None | 75 mg/mL PEG 400/ 3.8 mg/mL glycine |
| X | 3.5 | None | 100 mg/mL PEG 400/ 0.8 mg/mL glycine |
| Y | 3.6 | None | 20 mg/mL sucrose; 40 mg/mL mannitol/ 0.8 mg/mL glycine |
| Z | 3.6 | None | 28.5 mg/mL L-proline |
| AA | 3.6 | None | 100 mg/mL PEG 400/ 0.8 mg/mL glycine |
| BB | 3.75 | None | 9 mg/mL NaCl/ 3.8 mg/mL glycine |
| PP | 5.0 | 0.8 mg/mL sodium acetate trihydrate | 100 mg/mL PEG 400 |
| EE | 5.1 | 3.8 mg/mL sodium acetate trihydrate | 75 mg/mL PEG 400 |
| FF | 5.3 | 3.8 mg/mL sodium acetate trihydrate | 25 mg/mL glycerol |
| GG | 5.3 | 0.8 mg/mL acetate | 100 mg/mL PEG 400 |
| HH | 5.25 | 3.8 mg/mL sodium acetate trihydrate | 75 mg/mL PEG 400 |
| II | 5.25 | 3.8 mg/mL sodium acetate trihydrate | 25 mg/mL glycerol; alcohol |
| JJ | 5.25 | 3.8 mg/mL sodium acetate triydrate | 100 mg/mL sucrose |
| KK | 5.25 | 0.8 mg/mL sodium acetate trihydrate | 100 mg/mL PEG 400 |
| QQ | 5.5 | 0.8 mg/mL acetate | 100 mg/mL PEG 400 |
| MM | 5.75 | 28 mM acetate | 7.5% PEG 400 |
| OO | 3.6 | none | 28.5 mg/mL L-proline |

*Active is 2.5 mg/mL, rather than 5 mg/mL

The levels of degradants in the bivalirudin compositions including the impurity at relative retention time (RRT) of about 0.49, [12-20]-bivalirudin, [3-20]-bivalirudin, Asp 9-bivalirudin, [9-10]-cycloimido bivalirudin, [11-12]-cycloimido bivalirudin, and total impurities were measured at various time points as indicated. Various pH values were investigated, with a focus on the pH values between about 3.0 to less than 4.0, or 3.25 and 3.75, and 5.10 and 5.70, which the prior art teaches away from (see U.S. Pat. No. 7,803,762, Table 1). Additionally, various buffers, buffer strengths, stabilizers, amino acids and other tonicity-adjusting and/or stabilizing agents were used for approximately 50 individual formulations (not all data shown). For purposes of testing, stability determinations at 40° C./75% relative humidity (RH) for three days or 25° C./60% RH for 1 month were considered roughly equivalent and predictive of stability at 5° C. for 1 year, based on Arrhenius kinetics and the activation energies of the degradation pathways involved (Ea of about 20 to 25 kcal/mol).

For pH values in the range of about 3.0 to less than 4.0, or about 3.25 to about 3.75, and pH values in the range of 5.0 to about 5.7, representative degradant levels are expressed as % in tables below. The impurities are quantitatively determined by HPLC using very similar experimental conditions outlined in Example 21 of U.S. Pat. No. 7,803,762; however, the calculation of the percentage of each impurity was performed against a bivalirudin standard instead of as percent area under the curve (AUC). Conditions for the HPLC chromatographic analysis are as follows:

| Method Parameter | Condition/Criteria |
|---|---|
| Solution A | 0.05M Sodium Acetate solution in water adjusted to pH 6.5 ± 0.1 with dilute (2M) acetic acid. |
| Solution B | Solution A:Acetonitrile 50:50 |
| Diluent | Water |
| Standard concentration | 0.05 mg/mL Bivalirudin |
| Sample concentration | 2.5 mg/mL Bivalirudin |
| Column | Vydac C18 (250 × 4.6 mm), 5 µm; or equivalent |
| Flow rate | 1.2 mL/min |

| | Gradient Program | | |
|---|---|---|---|
| Gradient Program | Time (min) | Solution—A (% v/v) | Solution—B (% v/v) |
| | 0.01 | 90 | 10 |
| | 5 | 85 | 15 |
| | 30 | 65 | 35 |
| | 35 | 65 | 35 |
| | 35.01 | 90 | 10 |
| | 40 | 90 | 10 |

-continued

| Method Parameter | Condition/Criteria |
|---|---|
| Injection volume | 40 μL |
| Wavelength | 215 nm |
| Method Parameter | Condition/Criteria |
| Run time | 40 minutes |
| Column oven temperature | 40° C. |
| Autosampler temperature | 5° C. |

Degradants are abbreviated as follows, as will be understood by one of skill in the art, and with reference to this disclosure: "RRT 0.49" is the impurity at relative retention time of about 0.49, a bivalirudin fragment, previously identified in U.S. Pat. No. 7,803,762 as [1-11]-bivalirudin (SEQ ID NO:4), but identified instead as [5-20]-bivalirudin (SEQ ID NO:6) in some exemplary formulations of the present disclosure; "[12-20] BVN" is the bivalirudin fragment comprising residues 12-20 (SEQ ID NO:5); "[3-20] BVN" is the bivalirudin fragment comprising residues 3-20 (SEQ ID NO:2); "Asp 9-BVN" is the bivalirudin degradant having aspartic acid as residue 9 (SEQ ID NO:3); "[9-10] BVN" is the 9-10 cycloimido bivalirudin intermediate, and "[11-12] BVN" is the 11-12 cycloimido bivalirudin intermediate (see U.S. Pat. No. 7,803,762). According to the HPLC protocol detailed above, the relative retention times of degradants were observed in Table 3 as follows:

TABLE 3

Bivalirudin Impurities Observed at Approximate Relative Retention Times

| Impurity | Approximate RRT (within ±0.02 units) |
|---|---|
| [12-20] BVN | 0.55 |
| [3-20] BVN | 0.62 |
| Asp$^9$-BVN | 0.91 |

TABLE 3-continued

Bivalirudin Impurities Observed at Approximate Relative Retention Times

| Impurity | Approximate RRT (within ±0.02 units) |
|---|---|
| [9-10] BVN | 1.08 |
| [11-12] BVN | 1.36 |

Example 3: Stability Testing at 40° C./75% RH

Table 4 displays stability data of exemplary formulations of this invention at 40° C. and 75% relative humidity after three days or seven days. Initial values (t=0) determined at the time of manufacture are listed above the 3-day and 7-day data. Notably, the data show a suppression of the known and unknown impurities in the formulations having a pH in the range of about 3.0 to less than 4.0, or from about 3.25 to about 3.75, and at pH in the range of from above or equal to 5.0 to about 5.7. As shown in Table 4, the levels of degradants after storage for three days at 40° C. in the exemplary formulations with pH of about 3.0 to less than 4.0, or about 3.25 to about 3.75 pH range and the greater than or equal to 5.0 to about 5.7 pH range are surprisingly and significantly lower than those reported in U.S. Pat. No. 7,803,762, Tables 38-57, pH of 4 to less than 5 (where for example total impurities ranged from about 6.5% to 7.7% after three days at 40° C.). As also shown in Table 4, the levels of degradants after storage for seven days at 40° C. in the exemplary formulations with pH of about 3.0 to less than 4.0, or about 3.25 to about 3.75 pH range and the greater than or equal to 5 to about 5.7 pH range are surprisingly lower than those reported in U.S. Pat. No. 7,803,762, Tables 38-57, pH of 4 to less than 5 (where for example total impurities ranged from about 12.7% to 14.3% after seven days at 40° C.). Multiple data sets for a given formulation in all tables below (i.e., G1, G2, H1, H2, K1, K2, K3, S1 and S2) were based on independent analysis of separate batches of the same formulation.

TABLE 4

Stability Testing of Exemplary Formulations Performed at 40° C.

| Formulation (pH) | Time Point | RRT 0.49 | [12-20]-BVN | [3-20]-BVN | Asp$^9$-BVN | [9-10]-BVN | [11-12]-BVN | Total |
|---|---|---|---|---|---|---|---|---|
| A | Initial | 0.02 | 0.06 | 0.01 | 0.04 | 0.01 | 0.00 | 0.25 |
| (pH 2.5) | 3 days | 1.37 | 2.25 | 0.18 | 0.64 | 0.17 | 0.39 | 5.65 |
| | 7 days | 2.90 | 5.41 | 0.38 | 1.30 | 0.38 | 0.85 | 12.98 |
| B | Initial | 0.01 | 0.05 | 0.01 | 0.03 | 0.01 | 0.00 | 0.16 |
| (pH 2.5) | 3 days | 1.34 | 2.07 | 0.27 | 0.37 | 0.15 | 0.55 | 5.18 |
| | 7 days | 2.83 | 5.14 | 0.58 | 0.69 | 0.36 | 1.21 | 12.08 |
| C | Initial | 0.01 | 0.05 | 0.01 | 0.03 | 0.01 | 0.00 | 0.26 |
| (pH 3.0) | 3 days | 1.19 | 1.96 | 0.23 | 0.20 | 0.16 | 0.63 | 4.72 |
| | 7 days | 2.62 | 4.64 | 0.51 | 0.35 | 0.35 | 1.43 | 10.72 |
| D | Initial | 0.01 | 0.04 | 0.01 | 0.03 | 0.01 | 0.00 | 0.17 |
| (pH 3.0) | 3 days | 1.21 | 1.85 | 0.48 | 0.28 | 0.18 | 0.88 | 5.50 |
| | 7 days | 2.56 | 4.72 | 0.99 | 0.47 | 0.40 | 1.88 | 12.35 |
| E | Initial | 0.01 | 0.04 | 0.01 | 0.02 | 0.05 | 0.01 | 0.23 |
| (pH 3.0) | 3 days | 1.46 | 2.51 | 0.25 | 0.32 | 0.22 | 0.69 | 6.06 |
| | 7 days | 3.06 | 4.67 | 0.43 | 0.49 | 0.37 | 1.20 | 10.72 |
| F | Initial | 0.01 | 0.03 | 0.01 | 0.03 | 0.06 | 0.02 | 0.24 |
| (pH 3.0) | 3 days | 1.45 | 2.40 | 0.65 | 0.36 | 0.23 | 1.06 | 7.39 |
| | 7 days | 2.47 | 4.63 | 1.05 | 0.60 | 0.40 | 1.80 | 12.97 |
| G1 | Initial | 0.03 | 0.04 | 0.02 | 0.03 | 0.07 | 0.02 | 0.37 |
| (pH 3.0) | 3 days | 1.24 | 1.70 | 0.19 | 0.33 | 0.13 | 0.43 | 4.42 |
| | 7 days | 2.32 | 3.73 | 0.36 | 0.58 | 0.28 | 0.93 | 9.12 |
| G2 | Initial | 0.05 | 0.10 | 0.02 | 0.07 | 0.05 | 0.01 | 0.44 |
| (pH 3.0) | 3 days | 1.16 | 1.67 | 0.22 | 0.28 | 0.16 | 0.55 | 4.21 |
| | 7 days | 2.17 | 3.58 | 0.41 | 0.40 | 0.30 | 1.16 | 8.76 |

TABLE 4-continued

Stability Testing of Exemplary Formulations Performed at 40° C.

| Formulation (pH) | Time Point | RRT 0.49 | [12-20]-BVN | [3-20]-BVN | Asp$^9$-BVN | [9-10]-BVN | [11-12]-BVN | Total |
|---|---|---|---|---|---|---|---|---|
| H2 | Initial | 0.01 | 0.05 | 0.02 | 0.04 | 0.07 | 0.03 | 0.27 |
| (pH 3.25) | 3 days | 0.86 | 1.46 | 0.23 | 0.12 | 0.16 | 0.72 | 3.87 |
| | 7 days | 2.04 | 3.42 | 0.53 | 0.22 | 0.33 | 1.62 | 9.14 |
| H1 | Initial | 0.03 | 0.04 | 0.02 | 0.03 | 0.07 | 0.01 | 0.33 |
| (pH 3.25) | 3 days | 1.07 | 1.58 | 0.22 | 0.21 | 0.16 | 0.56 | 4.12 |
| | 7 days | 2.09 | 3.42 | 0.42 | 0.31 | 0.29 | 1.24 | 8.41 |
| I | Initial | 0.01 | 0.05 | 0.02 | 0.03 | 0.01 | 0.03 | 0.30 |
| (pH 3.5) | 3 days | 0.88 | 1.63 | 0.33 | 0.11 | 0.22 | 0.95 | 4.45 |
| | 7 days | 2.02 | 3.94 | 0.73 | 0.17 | 0.44 | 2.13 | 10.38 |
| J | Initial | 0.01 | 0.04 | 0.01 | 0.03 | 0.01 | 0.00 | 0.16 |
| (pH 3.5) | 3 days | 1.14 | 1.76 | 0.46 | 0.20 | 0.10 | 0.92 | 5.09 |
| | 7 days | 1.45 | 4.41 | 0.95 | 0.35 | 0.42 | 2.04 | 11.73 |
| K1 | Initial | 0.01 | 0.04 | 0.02 | 0.02 | 0.06 | 0.02 | 0.25 |
| (pH 3.5) | 3 days | 0.88 | 1.66 | 0.34 | 0.09 | 0.22 | 1.03 | 4.64 |
| | 7 days | 2.00 | 3.84 | 0.74 | 0.15 | 0.45 | 2.24 | 10.28 |
| K4 | Initial | 0.03 | 0.04 | 0.02 | 0.03 | 0.06 | 0.02 | 0.33 |
| (pH 3.5) | 3 days | 0.78 | 1.31 | 0.30 | 0.12 | 0.20 | 0.87 | 3.91 |
| | 7 days | 1.53 | 2.76 | 0.59 | 0.14 | 0.37 | 1.85 | 7.77 |
| K5 | Initial | 0.04 | 0.10 | 0.02 | 0.07 | 0.04 | 0.01 | 0.44 |
| (pH 3.5) | 3 days | 0.85 | 1.41 | 0.29 | 0.17 | 0.20 | 0.84 | 3.96 |
| | 7 days | 1.64 | 2.97 | 0.56 | 0.18 | 0.38 | 1.77 | 8.08 |
| L | Initial | 0.01 | 0.04 | 0.01 | 0.02 | 0.06 | 0.02 | 0.25 |
| (pH 3.5) | 3 days | 0.90 | 1.74 | 0.32 | 0.09 | 0.20 | 0.97 | 4.74 |
| | 7 days | 2.06 | 4.00 | 0.69 | 0.15 | 0.41 | 2.09 | 10.55 |
| M | Initial | 0.01 | 0.04 | 0.01 | 0.02 | 0.07 | 0.02 | 0.25 |
| (pH 3.5) | 3 days | 0.88 | 1.67 | 0.33 | 0.09 | 0.21 | 1.01 | 4.61 |
| | 7 days | 2.06 | 3.93 | 0.75 | 0.16 | 0.47 | 2.22 | 10.53 |
| N | Initial | 0.01 | 0.04 | 0.01 | 0.02 | 0.05 | 0.02 | 0.25 |
| (pH 3.5) | 3 days | 0.82 | 1.59 | 0.32 | 0.08 | 0.22 | 0.99 | 4.44 |
| | 7 days | 1.94 | 3.74 | 0.74 | 0.15 | 0.48 | 2.19 | 10.15 |
| O | Initial | 0.01 | 0.04 | 0.01 | 0.02 | 0.05 | 0.02 | 0.24 |
| (pH 3.5) | 3 days | 0.94 | 1.91 | 0.43 | 0.10 | 0.32 | 1.26 | 5.64 |
| | 7 days | 1.75 | 3.44 | 0.76 | 0.12 | 0.44 | 2.20 | 9.87 |
| P | Initial | 0.01 | 0.04 | 0.01 | 0.02 | 0.06 | 0.02 | 0.24 |
| (pH 3.5) | 3 days | 1.15 | 1.97 | 0.81 | 0.13 | 0.29 | 1.48 | 6.78 |
| | 7 days | 1.95 | 3.66 | 1.42 | 0.22 | 0.48 | 2.54 | 12.30 |
| Q | Initial | 0.01 | 0.04 | 0.01 | 0.03 | 0.06 | 0.02 | 0.25 |
| (pH 3.5) | 3 days | 0.85 | 1.73 | 1.12 | 0.09 | 0.33 | 1.82 | 6.80 |
| | 7 days | 1.56 | 3.45 | 1.94 | 0.14 | 0.52 | 3.00 | 11.96 |
| R | Initial | 0.01 | 0.05 | 0.02 | 0.03 | 0.07 | 0.01 | 0.31 |
| (pH 3.5) | 3 days | 0.71 | 1.23 | 0.27 | 0.09 | 0.16 | 0.78 | 3.71 |
| | 7 days | 1.42 | 2.66 | 0.54 | 0.13 | 0.31 | 1.70 | 7.70 |
| S2 | Initial | 0.02 | 0.06 | 0.02 | 0.04 | 0.05 | 0.02 | 0.32 |
| (pH 3.5) | 7 days | 2.04 | 3.81 | 1.00 | 0.18 | 0.52 | 2.64 | 11.07 |
| S1 | Initial | 0.01 | 0.04 | 0.02 | 0.03 | 0.07 | 0.01 | 0.27 |
| (pH 3.5) | 3 days | 0.64 | 1.18 | 0.35 | 0.11 | 0.22 | 0.95 | 3.69 |
| | 7 days | 1.26 | 2.56 | 0.69 | 0.11 | 0.40 | 2.04 | 7.63 |
| T | Initial | 0.05 | 0.13 | 0.02 | 0.04 | 0.06 | 0.12 | 0.57 |
| (pH 3.5) | 3 days | 0.56 | 1.11 | 0.30 | 0.08 | 0.19 | 0.87 | 3.57 |
| | 7 days | 1.16 | 2.29 | 0.63 | 0.12 | 0.35 | 1.70 | 7.14 |
| U | Initial | 0.05 | 0.12 | 0.03 | 0.04 | 0.05 | 0.12 | 0.68 |
| (pH 3.5) | 3 days | 0.47 | 0.97 | 0.28 | 0.07 | 0.17 | 0.80 | 3.48 |
| | 7 days | 1.00 | 2.04 | 0.59 | 0.11 | 0.31 | 1.62 | 6.93 |
| V | Initial | 0.02 | 0.07 | 0.02 | 0.03 | 0.04 | 0.04 | 0.31 |
| (pH 3.5) | 7 days | 1.72 | 3.56 | 1.03 | 0.17 | 0.54 | 2.75 | 10.75 |
| W | Initial | 0.02 | 0.06 | 0.01 | 0.03 | 0.05 | 0.02 | 0.33 |
| (pH 3.5) | 7 days | 1.71 | 3.41 | 0.90 | 0.14 | 0.48 | 2.31 | 9.98 |
| BB | Initial | 0.03 | 0.04 | 0.02 | 0.03 | 0.08 | 0.0 | 0.37 |
| (pH 3.75) | 3 days | 0.58 | 1.13 | 0.40 | 0.09 | 0.25 | 1.08 | 3.81 |
| | 7 days | 1.12 | 2.38 | 0.80 | 0.11 | 0.46 | 2.25 | 7.72 |
| OO | Initial | 0.01 | 0.05 | 0.02 | 0.03 | 0.05 | 0.02 | 0.27 |
| (pH 3.8) | 7 days | 1.00 | 2.81 | 1.28 | 0.15 | 0.60 | 2.96 | 9.93 |
| EE | Initial | 0.00 | 0.04 | 0.03 | 0.03 | 0.04 | 0.02 | 0.28 |
| (pH 5.10) | 7 days | 0.69 | 0.58 | 3.79 | 1.05 | 1.88 | 1.80 | 11.54 |
| HH | Initial | 0.00 | 0.03 | 0.03 | 0.03 | 0.05 | 0.02 | 0.31 |
| (pH 5.25) | 7 days | 0.76 | 0.49 | 3.99 | 1.35 | 2.05 | 1.60 | 12.02 |
| II | Initial | 0.00 | 0.04 | 0.04 | 0.04 | 0.06 | 0.02 | 0.34 |
| (pH 5.25) | 7 days | 0.74 | 0.44 | 3.92 | 1.66 | 2.22 | 1.40 | 12.51 |
| JJ | Initial | 0.01 | 0.04 | 0.04 | 0.04 | 0.06 | 0.02 | 0.33 |
| (pH 5.25) | 7 days | 0.64 | 0.47 | 3.74 | 1.63 | 2.25 | 1.42 | 11.92 |
| MM | Initial | 0.00 | 0.04 | 0.04 | 0.03 | 0.09 | 0.01 | 0.34 |
| (pH 5.75) | 7 days | 1.01 | 0.17 | 4.54 | 4.52 | 3.01 | 0.64 | 16.35 |

Example 4: Stability Testing at 25° C.

Table 5a displays stability data of exemplary formulations of this invention at 25° C. and 65% relative humidity after one month. Initial values (t=0) determined at the time of manufacture are listed above the 1-month data. As previously noted, stability data after 1 month at 25° C. are roughly predictive of stability at 5° C. after 12 months.

TABLE 5a

Stability Testing of Exemplary Formulations Performed at 25° C.

| Formulation (pH) | Time Point | RRT 0.49 | [12-20]-BVN | [3-20]-BVN | $Asp^9$-BVN | [9-10]-BVN | [11-12]-BVN | Total |
|---|---|---|---|---|---|---|---|---|
| A | Initial | 0.02 | 0.06 | 0.01 | 0.04 | 0.01 | 0.00 | 0.25 |
| (pH 2.5) | 1 M | 1.98 | 3.33 | 0.20 | 1.11 | 0.23 | 0.62 | 9.26 |
| B | Initial | 0.01 | 0.05 | 0.01 | 0.03 | 0.01 | 0.00 | 0.16 |
| (pH 2.5) | 1 M | 2.26 | 3.60 | 0.29 | 0.62 | 0.22 | 0.92 | 9.42 |
| C | Initial | 0.01 | 0.05 | 0.01 | 0.03 | 0.01 | 0.00 | 0.26 |
| (pH 3.0) | 1 M | 1.77 | 2.83 | 0.27 | 0.30 | 0.22 | 1.13 | 7.30 |
| D | Initial | 0.01 | 0.04 | 0.01 | 0.03 | 0.01 | 0.00 | 0.17 |
| (pH 3.0) | 1 M | 1.76 | 2.94 | 0.52 | 0.45 | 0.25 | 1.49 | 8.62 |
| E | Initial | 0.01 | 0.04 | 0.01 | 0.02 | 0.05 | 0.01 | 0.23 |
| (pH 3.0) | 1 M | 1.72 | 2.80 | 0.24 | 0.48 | 0.20 | 0.91 | 7.01 |
| F | Initial | 0.01 | 0.03 | 0.01 | 0.03 | 0.06 | 0.02 | 0.24 |
| (pH 3.0) | 1 M | 1.71 | 2.94 | 0.55 | 0.56 | 0.26 | 1.45 | 8.63 |
| G1 | Initial | 0.03 | 0.04 | 0.02 | 0.03 | 0.07 | 0.02 | 0.37 |
| (pH 3.0) | 1 M | 1.82 | 2.99 | 0.24 | 0.61 | 0.21 | 0.87 | 7.58 |
| G2 | Initial | 0.05 | 0.10 | 0.02 | 0.07 | 0.05 | 0.01 | 0.44 |
| (pH 3.0) | 1 M | 1.68 | 2.77 | 0.27 | 0.46 | 0.24 | 1.07 | 7.14 |
| H1 | Initial | 0.03 | 0.04 | 0.02 | 0.03 | 0.07 | 0.01 | 0.33 |
| (pH 3.25) | 1 M | 1.66 | 2.69 | 0.28 | 0.37 | 0.15 | 1.14 | 6.90 |
| H2 | Initial | 0.01 | 0.05 | 0.02 | 0.04 | 0.07 | 0.03 | 0.27 |
| (pH 3.25) | 1 M | 1.64 | 2.79 | 0.35 | 0.20 | 0.27 | 1.50 | 7.31 |
| I | Initial | 0.01 | 0.05 | 0.02 | 0.03 | 0.01 | 0.03 | 0.30 |
| (pH 3.5) | 1 M | 1.42 | 2.42 | 0.38 | 0.14 | 0.28 | 1.65 | 7.02 |
| J | Initial | 0.01 | 0.04 | 0.01 | 0.03 | 0.01 | 0.00 | 0.16 |
| (pH 3.5) | 1 M | 1.69 | 2.73 | 0.50 | 0.33 | 0.25 | 1.57 | 8.12 |
| K1 | Initial | 0.01 | 0.04 | 0.02 | 0.02 | 0.06 | 0.02 | 0.25 |
| (pH 3.5) | 1 M | 1.30 | 2.25 | 0.38 | 0.16 | 0.28 | 1.62 | 6.40 |
| K4 | Initial | 0.03 | 0.04 | 0.02 | 0.03 | 0.06 | 0.02 | 0.33 |
| (pH 3.5) | 1 M | 1.20 | 2.19 | 0.39 | 0.16 | 0.29 | 1.69 | 6.35 |
| K5 | Initial | 0.04 | 0.10 | 0.02 | 0.07 | 0.04 | 0.01 | 0.44 |
| (pH 3.5) | 1 M | 1.24 | 2.28 | 0.37 | 0.20 | 0.30 | 1.59 | 6.43 |
| L | Initial | 0.01 | 0.04 | 0.01 | 0.02 | 0.06 | 0.02 | 0.25 |
| (pH 3.5) | 1 M | 1.36 | 2.38 | 0.37 | 0.17 | 0.26 | 1.53 | 6.82 |
| M | Initial | 0.01 | 0.04 | 0.01 | 0.02 | 0.07 | 0.02 | 0.25 |
| (pH 3.5) | 1 M | 1.47 | 2.32 | 0.39 | 0.17 | 0.31 | 1.64 | 6.56 |
| N | Initial | 0.01 | 0.04 | 0.01 | 0.02 | 0.05 | 0.02 | 0.25 |
| (pH 3.5) | 1 M | 1.32 | 2.31 | 0.38 | 0.17 | 0.29 | 1.63 | 6.52 |
| O | Initial | 0.01 | 0.04 | 0.01 | 0.02 | 0.05 | 0.02 | 0.24 |
| (pH 3.5) | 1 M | 1.14 | 2.12 | 0.40 | 0.16 | 0.22 | 1.66 | 6.23 |
| P | Initial | 0.01 | 0.04 | 0.01 | 0.02 | 0.06 | 0.02 | 0.24 |
| (pH 3.5) | 1 M | 1.46 | 2.24 | 0.76 | 0.22 | 0.29 | 2.03 | 8.00 |
| Q | Initial | 0.01 | 0.04 | 0.01 | 0.03 | 0.06 | 0.02 | 0.25 |
| (pH 3.5) | 1 M | 1.13 | 2.05 | 1.00 | 0.19 | 0.32 | 2.36 | 7.67 |
| R | Initial | 0.01 | 0.05 | 0.02 | 0.03 | 0.07 | 0.01 | 0.31 |
| (pH 3.5) | 1 M | 1.08 | 2.02 | 0.34 | 0.14 | 0.23 | 1.49 | 6.34 |
| S1 | Initial | 0.01 | 0.04 | 0.02 | 0.03 | 0.07 | 0.01 | 0.27 |
| (pH 3.5) | 1 M | 0.97 | 1.96 | 0.44 | 0.13 | 0.31 | 1.80 | 5.96 |
| S2 | Initial | 0.02 | 0.06 | 0.02 | 0.04 | 0.05 | 0.02 | 0.32 |
| (pH 3.5) | 1 M | 1.12 | 1.96 | 0.45 | 0.15 | 0.29 | 1.79 | 6.13 |
| T | Initial | 0.05 | 0.13 | 0.02 | 0.04 | 0.06 | 0.12 | 0.57 |
| (pH 3.5) | 1 M | 0.92 | 1.83 | 0.42 | 0.10 | 0.28 | 1.57 | 5.63 |
| U | Initial | 0.05 | 0.12 | 0.03 | 0.04 | 0.05 | 0.12 | 0.68 |
| (pH 3.5) | 1 M | 0.78 | 1.55 | 0.37 | 0.10 | 0.23 | 1.45 | 5.47 |
| V | Initial | 0.02 | 0.07 | 0.02 | 0.03 | 0.04 | 0.04 | 0.31 |
| (pH 3.5) | 1 M | 0.98 | 1.90 | 0.45 | 0.15 | 0.29 | 1.76 | 5.88 |
| W | Initial | 0.02 | 0.06 | 0.01 | 0.03 | 0.05 | 0.02 | 0.33 |
| (pH 3.5) | 1 M | 1.00 | 1.83 | 0.40 | 0.12 | 0.20 | 1.56 | 5.55 |
| X | Initial | 0.03 | 0.09 | 0.02 | 0.07 | 0.06 | 0.05 | 0.43 |
| (pH 3.5) | 1 M (U) | 0.97 | 1.83 | 0.47 | 0.13 | 0.30 | 1.72 | 5.93 |
|  | 1 M (I) | 0.98 | 1.82 | 0.46 | 0.13 | 0.30 | 1.72 | 5.93 |
| Y | Initial | 0.03 | 0.07 | 0.04 | 0.05 | 0.09 | 0.04 | 0.45 |
| (pH 3.6) | 1 M | 0.81 | 1.64 | 0.44 | 0.10 | 0.30 | 1.80 | 5.69 |
| Z | Initial | 0.02 | 0.08 | 0.03 | 0.05 | 0.08 | 0.08 | 0.42 |
| (pH 3.6) | 1 M | 0.77 | 1.69 | 0.49 | 0.11 | 0.33 | 1.90 | 5.71 |
| AA | Initial | 0.00 | 0.04 | 0.02 | 0.05 | 0.12 | 0.01 | 0.36 |
| (pH 3.6) | 1 M | 0.76 | 1.52 | 0.43 | 0.10 | 0.27 | 1.56 | 4.97 |
| BB | Initial | 0.03 | 0.04 | 0.02 | 0.03 | 0.08 | 0.01 | 0.37 |
| (pH 3.75) | 1 M | 0.89 | 1.87 | 0.53 | 0.12 | 0.36 | 2.04 | 6.26 |
| OO | Initial | 0.01 | 0.05 | 0.02 | 0.03 | 0.05 | 0.02 | 0.27 |
| (pH 3.8) | 1 M | 0.60 | 1.51 | 0.55 | 0.11 | 0.35 | 1.96 | 5.56 |

TABLE 5a-continued

Stability Testing of Exemplary Formulations Performed at 25° C.

| Formulation (pH) | Time Point | RRT 0.49 | [12-20]-BVN | [3-20]-BVN | Asp$^9$-BVN | [9-10]-BVN | [11-12]-BVN | Total |
|---|---|---|---|---|---|---|---|---|
| EE | Initial | 0.00 | 0.04 | 0.03 | 0.03 | 0.04 | 0.02 | 0.28 |
| (pH 5.10) | 1 M | 0.14 | 0.32 | 1.69 | 0.46 | 1.07 | 1.28 | 5.57 |
| HH | Initial | 0.00 | 0.03 | 0.03 | 0.03 | 0.05 | 0.02 | 0.31 |
| (pH 5.25) | 1 M | 0.16 | 0.28 | 1.81 | 0.61 | 1.21 | 1.15 | 5.90 |
| II | Initial | 0.00 | 0.04 | 0.04 | 0.04 | 0.06 | 0.02 | 0.34 |
| (pH 5.25) | 1 M | 0.16 | 0.25 | 1.80 | 0.74 | 1.30 | 1.02 | 6.02 |
| JJ | Initial | 0.01 | 0.04 | 0.04 | 0.04 | 0.06 | 0.02 | 0.33 |
| (pH 5.25) | 1 M | 0.13 | 0.26 | 1.64 | 0.72 | 1.30 | 1.00 | 5.72 |
| KK | Initial | 0.00 | 0.05 | 0.02 | 0.04 | 0.05 | 0.01 | 0.27 |
| (pH 5.25) | 1 M (U) | 0.03 | 0.30 | 1.90 | 0.62 | 1.18 | 1.21 | 6.11 |
|  | 1 M (I) | 0.03 | 0.32 | 1.99 | 0.65 | 1.23 | 1.26 | 6.36 |
| FF | Initial | 0.00 | 0.04 | 0.06 | 0.05 | 0.09 | 0.04 | 0.44 |
| (pH 5.3) | 1 M | 0.14 | 0.23 | 1.75 | 0.97 | 1.47 | 0.89 | 6.18 |
| GG | Initial | 0.00 | 0.05 | 0.03 | 0.06 | 0.05 | 0.02 | 0.30 |
| (pH 5.3) | 1 M | 0.02 | 0.26 | 1.78 | 0.54 | 1.14 | 1.16 | 5.77 |
| MM | Initial | 0.00 | 0.04 | 0.04 | 0.03 | 0.09 | 0.01 | 0.34 |
| (pH 5.75) | 1 M | 0.21 | 0.11 | 2.15 | 2.11 | 1.97 | 0.52 | 7.90 |

Notably, the 25° C. stability data also show a suppression of the known and unknown impurities in the formulations having a pH in the range of about 3.0 to less than 4.0, or from about 3.25 to about 3.75, and at pH in the range of from above or equal to 5.0 to about 5.7. As shown in Table 5a, the levels of degradants after storage for one month at 25° C. in the exemplary formulations with pH of about 3.0 to less than 4.0, or about 3.25 to about 3.75 pH range and the greater than or equal to 5.0 to about 5.7 pH range are surprisingly and significantly lower than those reported in U.S. Pat. No. 7,803,762, Table 1, (where extensive degradation ranging from 37.7% and 51.1% total impurities was observed at pH 3 to 4, respectively, and complete degradation was observed at both pH 5 and pH 6). As also shown in Table 5a, the levels of degradants after storage for 1 month at 25° C. in many of the exemplary formulations with pH of about 3.0 to less than 4.0, or about 3.25 to about 3.75 pH range and the greater than or equal to 5.0 to about 5.7 pH range are lower than those reported in U.S. Pat. No. 7,803,762, for formulations of pH of 4 to less than 5 (where for example total impurities ranged from about 5.1% to 9.3% after 1 month at 25° C.).

Example 5: Long Term Stability Testing at 2-8° C.

The long-term stability testing under refrigerated conditions (5° C. for up to 18 months) is presented in Table 5b. The standard data presentation is initial (time equal zero) and, 3-, 6-, 9-, 12-, or 18-month data, presented in a row in each data cell. If other or further months are reported for sampling, this is indicated in the left column below the formulation information. The initial values (at time zero) are always presented first.

TABLE 5b

Stability Testing of Exemplary Formulations Performed at 5° C.

| Formulation (pH) | Time Point | RRT 0.49 | [12-20]-BVN | [3-20]-BVN | Asp$^9$-BVN | [9-10]-BVN | [11-12]-BVN | Total |
|---|---|---|---|---|---|---|---|---|
| A | Initial | 0.02 | 0.06 | 0.01 | 0.04 | 0.01 | 0.00 | 0.25 |
| (pH 2.5) | 3 M | 0.43 | 0.78 | 0.02 | 0.36 | 0.06 | 0.17 | 2.24 |
| C | Initial | 0.01 | 0.05 | 0.01 | 0.03 | 0.01 | 0.00 | 0.26 |
| (pH 3.0) | 3 M | 0.37 | 0.66 | 0.06 | 0.11 | 0.06 | 0.33 | 1.81 |
|  | 6 M | 0.85 | 1.33 | 0.10 | 0.22 | 0.12 | 0.67 | 3.49 |
|  | 9 M | 1.35 | 2.10 | 0.16 | 0.29 | 0.17 | 1.06 | 5.52 |
| E | Initial | 0.01 | 0.04 | 0.01 | 0.02 | 0.05 | 0.01 | 0.23 |
| (pH 3.0) | 3 M | 0.43 | 0.65 | 0.04 | 0.14 | 0.10 | 0.27 | 1.78 |
| H1 | Initial | 0.03 | 0.04 | 0.02 | 0.03 | 0.07 | 0.01 | 0.33 |
| (pH 3.25) | 3 M | 0.39 | 0.67 | 0.06 | 0.13 | 0.07 | 0.38 | 1.99 |
| H2 | Initial | 0.01 | 0.05 | 0.02 | 0.04 | 0.07 | 0.03 | 0.27 |
| (pH 3.25) | 3 M | 0.39 | 0.65 | 0.08 | 0.11 | 0.08 | 0.49 | 2.03 |
| I | Initial | 0.01 | 0.05 | 0.02 | 0.03 | 0.01 | 0.03 | 0.30 |
| (pH 3.5) | 3 M | 0.32 | 0.59 | 0.08 | 0.06 | 0.08 | 0.49 | 1.80 |
|  | 6 M | 0.67 | 1.15 | 0.14 | 0.12 | 0.15 | 1.00 | 3.45 |
|  | 9 M | 1.04 | 1.73 | 0.21 | 0.14 | 0.21 | 1.52 | 5.07 |
| K1 | Initial | 0.01 | 0.04 | 0.02 | 0.02 | 0.06 | 0.02 | 0.25 |
| (pH 3.5) | 3 M | 0.31 | 0.53 | 0.06 | 0.06 | 0.11 | 0.47 | 1.65 |
|  | 6 M | 0.59 | 1.00 | 0.14 | 0.09 | 0.21 | 0.93 | 3.23 |
|  | 9 M | 0.88 | 1.45 | 0.19 | 0.11 | 0.21 | 1.30 | 4.40 |
| K4 | Initial | 0.03 | 0.04 | 0.02 | 0.03 | 0.06 | 0.02 | 0.33 |
| (pH 3.5) | 3 M | 0.31 | 0.56 | 0.09 | 0.07 | 0.09 | 0.56 | 1.95 |
|  | 6 M | 0.04 | 0.56 | 0.15 | 0.09 | 0.14 | 1.03 | 3.18 |
| L | Initial | 0.01 | 0.04 | 0.01 | 0.02 | 0.06 | 0.02 | 0.25 |

TABLE 5b-continued

Stability Testing of Exemplary Formulations Performed at 5° C.

| Formulation (pH) | Time Point | RRT 0.49 | [12-20]-BVN | [3-20]-BVN | Asp$^9$-BVN | [9-10]-BVN | [11-12]-BVN | Total |
|---|---|---|---|---|---|---|---|---|
| (pH 3.5) | 3 M | 0.33 | 0.58 | 0.08 | 0.06 | 0.09 | 0.52 | 1.92 |
|  | 6 M | 0.62 | 1.06 | 0.12 | 0.10 | 0.20 | 0.91 | 3.37 |
|  | 9 M | 0.91 | 1.50 | 0.17 | 0.11 | 0.15 | 1.26 | 4.72 |
|  | 12 M | 1.24 | 2.37 | 0.27 | 0.21 | 0.23 | 1.90 | 7.16 |
| M | Initial | 0.01 | 0.04 | 0.01 | 0.02 | 0.07 | 0.02 | 0.25 |
| (pH 3.5) | 6 M | 0.59 | 1.02 | 0.13 | 0.10 | 0.21 | 0.93 | 3.21 |
| N | Initial | 0.01 | 0.04 | 0.01 | 0.02 | 0.05 | 0.02 | 0.25 |
| (pH 3.5) | 6 M | 0.58 | 1.00 | 0.13 | 0.09 | 0.22 | 0.91 | 3.20 |
|  | 12 M | 1.18 | 2.22 | 0.26 | 0.23 | 0.28 | 1.91 | 6.48 |
| O | Initial | 0.01 | 0.04 | 0.01 | 0.02 | 0.05 | 0.02 | 0.24 |
| (pH 3.5) | 3 M | 0.27 | 0.49 | 0.06 | 0.04 | 0.07 | 0.51 | 1.56 |
|  | 6 M | 0.53 | 0.96 | 0.14 | 0.08 | 0.20 | 0.97 | 3.19 |
| P | Initial | 0.01 | 0.04 | 0.01 | 0.02 | 0.06 | 0.02 | 0.24 |
| (pH 3.5) | 6 M | 0.61 | 0.79 | 0.23 | 0.13 | 0.25 | 1.21 | 3.69 |
|  | 12 M | 1.32 | 2.08 | 0.55 | 0.28 | 0.30 | 2.42 | 7.67 |
| Q | Initial | 0.01 | 0.04 | 0.01 | 0.03 | 0.06 | 0.02 | 0.25 |
| (pH 3.5) | 6 M | 0.58 | 1.03 | 0.39 | 0.11 | 0.17 | 1.44 | 3.96 |
|  | 12 M | 1.12 | 1.87 | 0.75 | 0.17 | 0.30 | 2.69 | 7.26 |
| R | Initial | 0.01 | 0.05 | 0.02 | 0.03 | 0.07 | 0.01 | 0.31 |
| (pH 3.5) | 6 M | 0.05 | 0.43 | 0.13 | 0.09 | 0.12 | 0.91 | 3.71 |
| S1 | Initial | 0.01 | 0.04 | 0.02 | 0.03 | 0.07 | 0.01 | 0.27 |
| (pH 3.5) | 3 M | 0.37 | 0.66 | 0.09 | 0.07 | 0.09 | 0.59 | 2.07 |
| S2 | Initial | 0.02 | 0.06 | 0.02 | 0.04 | 0.05 | 0.02 | 0.32 |
| (pH 3.5) | 3 M | 0.29 | 0.52 | 0.12 | 0.07 | 0.10 | 0.59 | 1.92 |
|  | 5 M 21 days | 0.55 | 0.93 | 0.16 | 0.08 | 0.15 | 1.09 | 3.18 |
|  | 9 M | 1.03 | 1.72 | 0.26 | 0.18 | 0.25 | 1.78 | 6.17 |
| T | Initial | 0.05 | 0.13 | 0.02 | 0.04 | 0.06 | 0.12 | 0.57 |
| (pH 3.5) | 3 M | 0.25 | 0.45 | 0.09 | 0.07 | 0.09 | 0.52 | 1.66 |
|  | 6 M | 0.22 | 0.01 | 0.15 | 0.08 | 0.13 | 0.88 | 2.41 |
|  | 9 M | 0.69 | 1.25 | 0.23 | 0.10 | 0.19 | 1.42 | 4.21 |
| U | Initial | 0.05 | 0.12 | 0.03 | 0.04 | 0.05 | 0.12 | 0.68 |
| (pH 3.5) | 3 M | 0.21 | 0.39 | 0.09 | 0.06 | 0.07 | 0.47 | 1.55 |
|  | 4 M | 0.26 | 0.50 | 0.09 | 0.06 | 0.08 | 0.60 | 2.09 |
|  | 6 M | 0.15 | 0.66 | 0.13 | 0.07 | 0.10 | 0.79 | 2.69 |
|  | 9 M | 0.00 | 0.95 | 0.20 | 0.10 | 0.12 | 1.28 | 4.48 |
| V | Initial | 0.02 | 0.07 | 0.02 | 0.03 | 0.04 | 0.04 | 0.31 |
| (pH 3.5) | 3 M | 0.29 | 0.58 | 0.12 | 0.08 | 0.10 | 0.62 | 1.95 |
|  | 5 M 21 days | 0.55 | 1.04 | 0.15 | 0.05 | 0.12 | 1.14 | 3.25 |
|  | 9 M | 0.76 | 1.54 | 0.26 | 0.18 | 0.24 | 1.75 | 5.03 |
| W | Initial | 0.02 | 0.06 | 0.01 | 0.03 | 0.05 | 0.02 | 0.33 |
| (pH 3.5) | 3 M | 0.30 | 0.52 | 0.10 | 0.07 | 0.09 | 0.55 | 2.05 |
|  | 5 M 21 days | 0.47 | 0.82 | 0.13 | 0.07 | 0.11 | 0.89 | 2.72 |
|  | 9 M | 0.76 | 1.47 | 0.23 | 0.18 | 0.21 | 1.54 | 4.69 |
|  | 12 M | 0.85 | 1.46 | 0.26 | 0.14 | 0.20 | 0.79 | 4.09 |
|  | 15 M | 1.26 | 2.18 | 0.36 | 0.16 | 0.31 | 2.25 | 7.06 |
|  | 18 M | 0.08 | 2.76 | 0.47 | 0.17 | 0.37 | 2.72 | 8.68 |
| X | Initial | 0.03 | 0.09 | 0.02 | 0.07 | 0.06 | 0.05 | 0.43 |
| (pH 3.5) | 3 M (U) | 0.28 | 0.54 | 0.11 | 0.08 | 0.10 | 0.61 | 1.80 |
|  | 6 M (U) | 0.47 | 0.87 | 0.18 | 0.09 | 0.15 | 1.02 | 3.04 |
|  | 9 M (U) | 0.03 | 1.37 | 0.26 | 0.10 | 0.22 | 1.58 | 4.62 |
|  | 12 M (U) | 0.06 | 1.84 | 0.34 | 0.15 | 0.30 | 2.05 | 6.26 |
|  | 3 M (I) | 0.27 | 0.52 | 0.11 | 0.07 | 0.09 | 0.60 | 1.75 |
|  | 6 M (I) | 0.47 | 0.90 | 0.18 | 0.09 | 0.15 | 1.04 | 3.10 |
|  | 9 M (I) | 0.03 | 1.37 | 0.25 | 0.10 | 0.21 | 1.57 | 4.61 |
|  | 12 M (I) | 0.06 | 1.82 | 0.34 | 0.15 | 0.29 | 2.04 | 6.24 |
| Y | Initial | 0.03 | 0.07 | 0.04 | 0.05 | 0.09 | 0.04 | 0.45 |
| (pH 3.6) | 3 M | 0.22 | 0.47 | 0.11 | 0.11 | 0.11 | 0.63 | 1.83 |
| Z | Initial | 0.02 | 0.08 | 0.03 | 0.05 | 0.08 | 0.08 | 0.42 |
| (pH 3.6) | 3 M | 0.20 | 0.50 | 0.12 | 0.09 | 0.11 | 0.67 | 1.81 |
| AA | Initial | 0.00 | 0.04 | 0.02 | 0.05 | 0.12 | 0.01 | 0.36 |
| (pH 3.6) | 3 M | 0.20 | 0.44 | 0.07 | 0.10 | 0.11 | 0.55 | 1.67 |
|  | 5 M 08 days | 0.02 | 0.66 | 0.14 | 0.08 | 0.13 | 0.84 | 2.43 |
|  | 9 M | 0.66 | 1.19 | 0.24 | 0.11 | 0.22 | 1.45 | 4.17 |
|  | 12 M | 0.01 | 1.65 | 0.34 | 0.12 | 0.23 | 1.93 | 5.52 |
| BB | Initial | 0.03 | 0.04 | 0.02 | 0.03 | 0.08 | 0.01 | 0.37 |
| (pH 3.75) | 3 M | 0.23 | 0.48 | 0.11 | 0.06 | 0.11 | 0.69 | 1.88 |
|  | 9 M | 0.68 | 1.28 | 0.28 | 0.09 | 0.25 | 1.79 | 4.77 |
| OO | Initial | 0.01 | 0.05 | 0.02 | 0.03 | 0.05 | 0.02 | 0.27 |
| (pH 3.8) | 3 M | 0.17 | 0.48 | 0.13 | 0.06 | 0.12 | 0.69 | 1.80 |
|  | 5 M 21 days | 0.33 | 0.74 | 0.19 | 0.06 | 0.22 | 1.17 | 3.01 |
|  | 9 M | 0.51 | 1.22 | 0.32 | 0.14 | 0.13 | 1.86 | 4.41 |

TABLE 5b-continued

Stability Testing of Exemplary Formulations Performed at 5° C.

| Formulation (pH) | Time Point | RRT 0.49 | [12-20]-BVN | [3-20]-BVN | Asp$^9$-BVN | [9-10]-BVN | [11-12]-BVN | Total |
|---|---|---|---|---|---|---|---|---|
| PP (pH 5.0) | Initial | — | 0.05 | BQL | 0.04 | 0.04 | BQL | 0.12 |
| | 3 M | — | 0.15 | 0.30 | 0.07 | 0.27 | 0.60 | 1.43 |
| | 6 M | — | 0.25 | 0.59 | 0.16 | 0.49 | 1.12 | 2.79 |
| EE (pH 5.10) | Initial | 0.00 | 0.04 | 0.03 | 0.03 | 0.04 | 0.02 | 0.28 |
| | 3 M | 0.02 | 0.12 | 0.37 | 0.10 | 0.38 | 0.51 | 1.76 |
| | 5 M 21 days | 0.02 | 0.18 | 0.60 | 0.16 | 0.58 | 0.82 | 2.67 |
| | 9 M | 0.04 | 0.27 | 1.00 | 0.39 | 0.82 | 1.19 | 4.07 |
| | 12 M | 0.03 | 0.28 | 1.09 | 0.47 | 0.75 | 0.55 | 4.09 |
| | 15 M | 0.05 | 0.39 | 1.46 | 0.72 | 1.03 | 1.46 | 5.77 |
| | 18 M | 0.02 | 0.50 | 1.83 | 0.95 | 1.13 | 1.64 | 6.92 |
| HH (pH 5.25) | Initial | 0.00 | 0.03 | 0.03 | 0.03 | 0.05 | 0.02 | 0.31 |
| | 3 M | 0.02 | 0.09 | 0.41 | 0.11 | 0.44 | 0.46 | 1.88 |
| | 5 M 21 days | 0.02 | 0.16 | 0.65 | 0.19 | 0.80 | 0.76 | 2.95 |
| | 9 M | 0.05 | 0.20 | 1.07 | 0.51 | 0.92 | 1.05 | 4.21 |
| II (pH 5.25) | Initial | 0.00 | 0.04 | 0.04 | 0.04 | 0.06 | 0.02 | 0.34 |
| | 3 M | 0.02 | 0.09 | 0.39 | 0.13 | 0.48 | 0.41 | 1.79 |
| | 5 M 21 days | 0.02 | 0.14 | 0.61 | 0.23 | 0.68 | 0.62 | 2.60 |
| | 9 M | 0.07 | 0.22 | 1.06 | 0.63 | 1.00 | 0.94 | 4.26 |
| JJ (pH 5.25) | Initial | 0.01 | 0.04 | 0.04 | 0.04 | 0.06 | 0.02 | 0.33 |
| | 3 M | 0.02 | 0.09 | 0.36 | 0.13 | 0.50 | 0.40 | 1.85 |
| KK (pH 5.25) | Initial | 0.00 | 0.05 | 0.02 | 0.04 | 0.05 | 0.01 | 0.27 |
| | 3 M (U) | 0.01 | 0.12 | 0.43 | 0.12 | 0.41 | 0.50 | 1.71 |
| | 6 M (U) | 0.00 | 0.17 | 0.70 | 0.24 | 0.63 | 0.77 | 2.80 |
| | 9 M (U) | 0.04 | 0.24 | 1.06 | 0.44 | 0.85 | 1.08 | 4.12 |
| | 12 M (U) | 0.11 | 0.32 | 1.40 | 0.70 | 1.03 | 1.26 | 5.33 |
| | 15 M (U) | 0.11 | 0.34 | 1.55 | 0.79 | 1.08 | 1.35 | 5.81 |
| | 18 M (U) | 0.13 | 0.41 | 1.77 | 1.05 | 1.11 | 1.46 | 6.52 |
| | 3 M (I) | 0.01 | 0.12 | 0.42 | 0.12 | 0.37 | 0.49 | 1.63 |
| | 6 M (I) | 0.00 | 0.17 | 0.70 | 0.24 | 0.63 | 0.77 | 2.80 |
| | 9 M (I) | 0.03 | 0.24 | 1.07 | 0.44 | 0.85 | 1.08 | 4.14 |
| | 12 M (I) | 0.11 | 0.32 | 1.38 | 0.68 | 1.02 | 1.26 | 5.28 |
| | 15 M (I) | 0.11 | 0.34 | 1.54 | 0.79 | 1.06 | 1.46 | 5.77 |
| | 18 M (I) | 0.13 | 0.41 | 1.77 | 1.05 | 1.10 | 1.46 | 6.51 |
| FF (pH 5.3) | Initial | 0.00 | 0.04 | 0.06 | 0.05 | 0.09 | 0.04 | 0.44 |
| | 3 M | 0.02 | 0.07 | 0.40 | 0.21 | 0.57 | 0.37 | 1.85 |
| GG (pH 5.3) | Initial | 0.00 | 0.05 | 0.03 | 0.06 | 0.05 | 0.02 | 0.30 |
| | 3 M | 0.00 | 0.10 | 0.37 | 0.12 | 0.46 | 0.45 | 1.61 |
| | 5 M 09 days | 0.02 | 0.13 | 0.56 | 0.19 | 0.56 | 0.63 | 2.35 |
| | 9 M | 0.02 | 0.21 | 0.95 | 0.41 | 0.81 | 0.97 | 3.82 |
| | 12 M | 0.07 | 0.28 | 1.32 | 0.61 | 0.95 | 1.24 | 4.94 |
| QQ (pH 5.50) | Initial | — | 0.05 | BQL | 0.04 | 0.04 | BQL | 0.12 |
| | 3 M | — | 0.09 | 0.40 | 0.14 | 0.49 | 0.39 | 1.57 |
| | 6 M | — | 0.14 | 0.79 | 0.38 | 0.79 | 0.72 | 3.01 |
| MM (pH 5.75) | Initial | 0.00 | 0.04 | 0.04 | 0.03 | 0.09 | 0.01 | 0.34 |
| | 3 M | 0.02 | 0.05 | 0.50 | 0.33 | 0.85 | 0.23 | 2.25 |

For example, the increase in the amount of total impurities as compared to an initial time point, as determined by high performance liquid chromatography ("HPLC") at a wavelength of 215 nm, remains well under about 10%, under about 7.5% and under about 6.5% after storage at 5° C. for 12 months, for the samples having pH in the range of about 3.0 to less than 4.0, or about 3.25 to about 3.75. Also, the increase in the amount of total impurities as compared to an initial time point remains well under about 8%, under about 7.5%, under about 6.5% and under about 5% after storage at 5° C. for 12 months, for the samples having pH in the range of 5.0 to about 5.7.

Moreover, the increase in Asp 9-bivalirudin % and [9-10]-cycloimido-bivalirudin %, as determined by high performance liquid chromatography (HPLC) at 215 nm, as compared to an initial value (for example, at the time of manufacture of the formulation) remains well under about 1.0%, under about 0.5%, under about 0.4%, under about 0.3%, and under about 0.25% after storage at 5° C. for 12 months, for the samples having pH in the range of about 3.0 to less than 4.0, or about 3.25 to about 3.75. The increase in [3-20]-bivalirudin % and [9-10]-cycloimido-bivalirudin, as determined by high performance liquid chromatography (HPLC) at 215 nm, as compared to an initial value remains well under about well under about 1.0%, or under about 0.5% after storage at 5° C. for 12 months. The increase in [12-20]-bivalirudin and [11-12]-cycloimido-bivalirudin as compared to an initial value remains well under about well under about 3%, or under about 2.5%, or under about 2.0% after storage at 5° C. for 12 months.

The increase in the amount of Asp 9-bivalirudin % area under the curve from an initial value remains well under about 1.5%, under about 1.0%, under about 0.75% and under about 0.6% after storage at 5° C. for 12 months, for the samples having pH in the range of 5.0 to about 5.7. Also, the increase in the amount of the [3-20]-bivalirudin impurity as compared to an initial time point remains well under about 1.8%, or under 1.5% after storage at 5° C. for 12 months, for the samples having pH in the range of 5.0 to about 5.7. Also, the increases in the amount of the [11-12]-cycloimido-bivalirudin and the [9-10]-cycloimido-bivalirudin impurity as compared to an initial time point remains well under about 2.0%, or under about 1.6%, after storage at 5° C. for 12 months, for the samples having pH in the range of 5.0 to about 5.7.

These formulations described and taught herein provide storage stable, ready-to-use bivalirudin formulations. The formulations described herein and characterized in Table 5b show high stability over 6 months, or 9 months, or 12 months or more at 2-8° C.

Example 6: pH Variation at pH of about 2.5 to 3.5

Data presented in Tables 6a and 6b shows an investigation into the influence of pH on the stability (5° C. for 3 months; and 25° C./60% RH, respectively) of various bivalirudin formulations with 50 mM glycine, in the about 2.5 to about 3.5 pH range. The initial values are reported first in each data cell of Table 6a and Table 6b, followed by the available stability data for each formulation.

TABLE 6a

Stability Testing pH Variation, 3-month (repeated) Data at 5° C.

| Formulation (pH) | Time Point | RRT 0.49 | [12-20]-BVN | [3-20]-BVN | $Asp^9$-BVN | [9-10]-BVN | [11-12]-BVN | Total |
|---|---|---|---|---|---|---|---|---|
| A | Initial | 0.02 | 0.06 | 0.01 | 0.04 | 0.01 | 0.00 | 0.25 |
| (pH 2.5) | 3 M | 0.43 | 0.78 | 0.02 | 0.36 | 0.06 | 0.17 | 2.24 |
| C | Initial | 0.01 | 0.05 | 0.01 | 0.03 | 0.01 | 0.00 | 0.26 |
| (pH 3.0) | 3 M | 0.37 | 0.66 | 0.06 | 0.11 | 0.06 | 0.33 | 1.81 |
| | 6 M | 0.85 | 1.33 | 0.10 | 0.22 | 0.12 | 0.67 | 3.49 |
| | 9 M | 1.35 | 2.10 | 0.16 | 0.29 | 0.17 | 1.06 | 5.52 |
| I | Initial | 0.01 | 0.05 | 0.02 | 0.03 | 0.01 | 0.03 | 0.30 |
| (pH 3.5) | 3 M | 0.32 | 0.59 | 0.08 | 0.06 | 0.08 | 0.49 | 1.80 |
| | 6 M | 0.67 | 1.15 | 0.14 | 0.12 | 0.15 | 1.00 | 3.45 |
| | 9 M | 1.04 | 1.73 | 0.21 | 0.14 | 0.21 | 1.52 | 5.07 |

TABLE 6b

Stability Testing pH Variation, 1-month Data at 25° C./60% RH

| Formulation (pH) | Time Point | RRT 0.49 | [12-20]-BVN | [3-20]-BVN | $Asp^9$-BVN | [9-10]-BVN | [11-12]-BVN | Total |
|---|---|---|---|---|---|---|---|---|
| A | Initial | 0.02 | 0.06 | 0.01 | 0.04 | 0.01 | 0.00 | 0.25 |
| (pH 2.5) | 1 M | 1.98 | 3.33 | 0.20 | 1.11 | 0.23 | 0.62 | 9.26 |
| C | Initial | 0.01 | 0.05 | 0.01 | 0.03 | 0.01 | 0.00 | 0.26 |
| (pH 3.0) | 1 M | 1.77 | 2.83 | 0.27 | 0.30 | 0.22 | 1.13 | 7.30 |
| I | Initial | 0.01 | 0.05 | 0.02 | 0.03 | 0.01 | 0.03 | 0.30 |
| (pH 3.5) | 1 M | 1.42 | 2.42 | 0.38 | 0.14 | 0.28 | 1.65 | 7.02 |

As can be seen from the data in Tables 6a and 6b, the pH value of about 3.0 to about 3.5 provides an acceptable environment to effectively stabilize liquid bivalirudin formulations, contrary to the data reported in U.S. Pat. No. 7,803,762, Table 1.

Example 7: Effect of Buffer at pH of about 2.5 to 3.5

Although glycine was used in the formulations of Example 6, it only provides a buffering effect in the pH range of about ±1 unit about its $pK_{a1}$ (2.34). Table 7 presents the results of an investigation into the influence of buffer type on the stability (25° C./60% RH for 1 month) of various bivalirudin formulations, using a citrate:phosphate buffer (25 mM citrate; 15 mM phosphate) that provides buffering over the full target pH range of about 2.5 to about 3.5 pH range ($pK_{a1}$ of 3.15 and 2.15 respectively). The initial values are reported first in each data cell of Table 7, followed by the available stability data for each formulation.

TABLE 7

Stability Testing Buffer Variation, 1-month Data at 25° C./60% RH

| Formulation (pH) | Time Point | RRT 0.49 | [12-20]-BVN | [3-20]-BVN | $Asp^9$-BVN | [9-10]-BVN | [11-12]-BVN | Total |
|---|---|---|---|---|---|---|---|---|
| B | Initial | 0.01 | 0.05 | 0.01 | 0.03 | 0.01 | 0.00 | 0.16 |
| (pH 2.5) | 1 M | 2.26 | 3.60 | 0.29 | 0.62 | 0.22 | 0.92 | 9.42 |
| D | Initial | 0.01 | 0.04 | 0.01 | 0.03 | 0.01 | 0.00 | 0.17 |
| (pH 3.0) | 1 M | 1.76 | 2.94 | 0.52 | 0.45 | 0.25 | 1.49 | 8.62 |
| J | Initial | 0.01 | 0.04 | 0.01 | 0.03 | 0.01 | 0.00 | 0.16 |
| (pH 3.5) | 1 M | 1.69 | 2.73 | 0.50 | 0.33 | 0.25 | 1.57 | 8.12 |

As can be seen from the data in Table 7, the citrate-phosphate buffer provides an acceptable environment for the effective stabilization of liquid bivalirudin formulations, although the glycine formulations of Example 6 are slightly better at pH 3.0 and pH 3.5.

Example 8: Tonicity Agent Variation at pH 3.5

Tables 8a and 8b display the results of an investigation into the influence of various tonicity agents on the refrigerated stability (5° C. for 3 months, and 25° C./60% RH, respectively) of various bivalirudin formulations at about pH 3.5. The initial values (t=0) are reported first in each data cell of Tables 8a and 8b, and the following values were from data points taken at various times (1-, 3-, 6-, 9- or 12-months).

TABLE 8a

Stability Testing, tonicity agent variation, various month data at 5° C.

| Formulation (pH) | Time Point | RRT 0.49 | [12-20]-BVN | [3-20]-BVN | $Asp^9$-BVN | [9-10]-BVN | [11-12]-BVN | Total |
|---|---|---|---|---|---|---|---|---|
| K1 | Initial | 0.01 | 0.04 | 0.02 | 0.02 | 0.06 | 0.02 | 0.25 |
| (pH 3.5) | 3 M | 0.31 | 0.53 | 0.06 | 0.06 | 0.11 | 0.47 | 1.65 |
| | 6 M | 0.59 | 1.00 | 0.14 | 0.09 | 0.21 | 0.93 | 3.23 |
| | 9 M | 0.88 | 1.45 | 0.19 | 0.11 | 0.21 | 1.30 | 4.40 |
| K4 | Initial | 0.03 | 0.04 | 0.02 | 0.03 | 0.06 | 0.02 | 0.33 |
| (pH 3.5) | 3 M | 0.31 | 0.56 | 0.09 | 0.07 | 0.09 | 0.56 | 1.95 |
| | 6 M | 0.04 | 0.56 | 0.15 | 0.09 | 0.14 | 1.03 | 3.18 |
| L | Initial | 0.01 | 0.04 | 0.01 | 0.02 | 0.06 | 0.02 | 0.25 |
| (pH 3.5) | 3 M | 0.33 | 0.58 | 0.08 | 0.06 | 0.09 | 0.52 | 1.92 |
| | 6 M | 0.62 | 1.06 | 0.12 | 0.10 | 0.20 | 0.91 | 3.37 |
| | 9 M | 0.91 | 1.50 | 0.17 | 0.11 | 0.15 | 1.26 | 4.72 |
| | 12 M | 1.24 | 2.37 | 0.27 | 0.21 | 0.23 | 1.90 | 7.16 |

TABLE 8b

Stability Testing, tonicity agent variation, 1-month data at 25° C./60% RH

| Formulation (pH) | Time Point | RRT 0.49 | [12-20]-BVN | [3-20]-BVN | $Asp^9$-BVN | [9-10]-BVN | [11-12]-BVN | Total |
|---|---|---|---|---|---|---|---|---|
| K1 | Initial | 0.01 | 0.04 | 0.02 | 0.02 | 0.06 | 0.02 | 0.25 |
| (pH 3.5) | 1 M | 1.30 | 2.25 | 0.38 | 0.16 | 0.28 | 1.62 | 6.40 |
| K4 | Initial | 0.03 | 0.04 | 0.02 | 0.03 | 0.06 | 0.02 | 0.33 |
| (pH 3.5) | 1 M | 1.20 | 2.19 | 0.39 | 0.16 | 0.29 | 1.69 | 6.35 |
| K5 | Initial | 0.04 | 0.10 | 0.02 | 0.07 | 0.04 | 0.01 | 0.44 |
| (pH 3.5) | 1 M | 1.24 | 2.28 | 0.37 | 0.20 | 0.30 | 1.59 | 6.43 |
| L | Initial | 0.01 | 0.04 | 0.01 | 0.02 | 0.06 | 0.02 | 0.25 |
| (pH 3.5) | 1 M | 1.36 | 2.38 | 0.37 | 0.17 | 0.26 | 1.53 | 6.82 |

As can be seen from the data in Tables 8a and 8b, the tonicity agents chosen are useful to stabilize liquid bivalirudin formulations, as measured at pH of about 3.5.

Example 9: pH Variation with Stabilizer/Tonicity Agent

Data presented in Tables 9a and 9b shows an investigation into the influence of pH on the stability (at 5° C. for various numbers of months, and at 25° C./60% RH for one month, respectively) of various bivalirudin formulations having 0.9% NaCl as tonicity agent, in the about 2.5 to about 3.5 pH range, and having 7.5% PEG 400 as a stabilizer/tonicity agent, and at 28 mM buffer strength (3.8 mg/mL sodium acetate trihydrate) in the 5.0 up to about 5.7 pH range. The initial values are reported first in each data cell of Tables 9a and 9b, and the other values were from data points of various months, as reported in Tables 9a and 9b.

TABLE 9a pH variation with Stabilizer/Tonicity Agent at 5° C.

| Formulation (pH) | Time Point | RRT 0.49 | [12-20]-BVN | [3-20]-BVN | Asp$^9$-BVN | [9-10]-BVN | [11-12]-BVN | Total |
|---|---|---|---|---|---|---|---|---|
| H1 | Initial | 0.03 | 0.04 | 0.02 | 0.03 | 0.07 | 0.01 | 0.33 |
| (pH 3.25) | 3 M | 0.39 | 0.67 | 0.06 | 0.13 | 0.07 | 0.38 | 1.99 |
| H2 | Initial | 0.01 | 0.05 | 0.02 | 0.04 | 0.07 | 0.03 | 0.27 |
| (pH 3.25) | 3 M | 0.39 | 0.65 | 0.08 | 0.11 | 0.08 | 0.49 | 2.03 |
| K1 | Initial | 0.01 | 0.04 | 0.02 | 0.02 | 0.06 | 0.02 | 0.25 |
| (pH 3.5) | 3 M | 0.31 | 0.53 | 0.06 | 0.06 | 0.11 | 0.47 | 1.65 |
|  | 6 M | 0.59 | 1.00 | 0.14 | 0.09 | 0.21 | 0.93 | 3.23 |
|  | 9 M | 0.88 | 1.45 | 0.19 | 0.11 | 0.21 | 1.30 | 4.40 |
| K4 | Initial | 0.03 | 0.04 | 0.02 | 0.03 | 0.06 | 0.02 | 0.33 |
| (pH 3.5) | 3 M | 0.31 | 0.56 | 0.09 | 0.07 | 0.09 | 0.56 | 1.95 |
|  | 6 M | 0.04 | 0.56 | 0.15 | 0.09 | 0.14 | 1.03 | 3.18 |
| BB | Initial | 0.03 | 0.04 | 0.02 | 0.03 | 0.08 | 0.01 | 0.37 |
| (pH 3.75) | 3 M | 0.23 | 0.48 | 0.11 | 0.06 | 0.11 | 0.69 | 1.88 |
|  | 6 M | 5.08 | 3.36 | 0.28 | 0.10 | 0.16 | 1.20 | 11.11 |
|  | 9 M | 0.68 | 1.28 | 0.28 | 0.09 | 0.25 | 1.79 | 4.77 |
| CC | Initial | 0.02 | 0.04 | 0.02 | 0.03 | 0.07 | 0.02 | 0.34 |
| (pH 4.0) | 3 M | 0.16 | 0.36 | 0.12 | 0.05 | 0.14 | 0.68 | 1.69 |
|  | 6 M | 1.87 | 1.09 | 0.06 | 0.05 | 0.24 | 1.25 | 5.10 |
|  | 9 M | 0.47 | 0.96 | 0.32 | 0.09 | 0.33 | 1.80 | 4.32 |
| EE | Initial | 0.00 | 0.04 | 0.03 | 0.03 | 0.04 | 0.02 | 0.28 |
| (pH 5.10) | 3 M | 0.02 | 0.12 | 0.37 | 0.10 | 0.38 | 0.51 | 1.76 |
|  | 5 M 21 days | 0.02 | 0.18 | 0.60 | 0.16 | 0.58 | 0.82 | 2.67 |
|  | 9 M | 0.04 | 0.27 | 1.00 | 0.39 | 0.82 | 1.19 | 4.07 |
|  | 12 M | 0.03 | 0.28 | 1.09 | 0.47 | 0.75 | 0.55 | 4.09 |
|  | 15 M | 0.05 | 0.39 | 1.46 | 0.72 | 1.03 | 1.46 | 5.77 |
|  | 18 M | 0.02 | 0.50 | 1.83 | 0.95 | 1.13 | 1.64 | 6.92 |
| HH | Initial | 0.00 | 0.03 | 0.03 | 0.03 | 0.05 | 0.02 | 0.31 |
| (pH 5.25) | 3 M | 0.02 | 0.09 | 0.41 | 0.11 | 0.44 | 0.46 | 1.88 |
|  | 5 M 21 days | 0.02 | 0.16 | 0.65 | 0.19 | 0.80 | 0.76 | 2.95 |
|  | 9 M | 0.05 | 0.20 | 1.07 | 0.51 | 0.92 | 1.05 | 4.21 |
| MM | Initial | 0.00 | 0.04 | 0.04 | 0.03 | 0.09 | 0.01 | 0.34 |
| (pH 5.75) | 3 M | 0.02 | 0.05 | 0.50 | 0.33 | 0.85 | 0.23 | 2.25 |

TABLE 9b pH variation with Stabilizer/Tonicity Agent at 25° C./60% RH

| Formulation (pH) | Time Point | RRT 0.49 | [12-20]-BVN | [3-20]-BVN | Asp$^9$-BVN | [9-10]-BVN | [11-12]-BVN | Total |
|---|---|---|---|---|---|---|---|---|
| G1 | Initial | 0.03 | 0.04 | 0.02 | 0.03 | 0.07 | 0.02 | 0.37 |
| (pH 3.0) | 1 M | 1.82 | 2.99 | 0.24 | 0.61 | 0.21 | 0.87 | 7.58 |
| G2 | Initial | 0.05 | 0.10 | 0.02 | 0.07 | 0.05 | 0.01 | 0.44 |
| (pH 3.0) | 1 M | 1.68 | 2.77 | 0.27 | 0.46 | 0.24 | 1.07 | 7.14 |
| H1 | Initial | 0.03 | 0.04 | 0.02 | 0.03 | 0.07 | 0.01 | 0.33 |
| (pH 3.25) | 1 M | 1.66 | 2.69 | 0.28 | 0.37 | 0.15 | 1.14 | 6.90 |
| H2 | Initial | 0.01 | 0.05 | 0.02 | 0.04 | 0.07 | 0.03 | 0.27 |
| (pH 3.25) | 1 M | 1.64 | 2.79 | 0.35 | 0.20 | 0.27 | 1.50 | 7.31 |
| K1 | Initial | 0.01 | 0.04 | 0.02 | 0.02 | 0.06 | 0.02 | 0.25 |
| (pH 3.5) | 1 M | 1.30 | 2.25 | 0.38 | 0.16 | 0.28 | 1.62 | 6.40 |
| K4 | Initial | 0.03 | 0.04 | 0.02 | 0.03 | 0.06 | 0.02 | 0.33 |
| (pH 3.5) | 1 M | 1.20 | 2.19 | 0.39 | 0.16 | 0.29 | 1.69 | 6.35 |
| K5 | Initial | 0.04 | 0.10 | 0.02 | 0.07 | 0.04 | 0.01 | 0.44 |
| (pH 3.5) | 1 M | 1.24 | 2.28 | 0.37 | 0.20 | 0.30 | 1.59 | 6.43 |
| BB | Initial | 0.03 | 0.04 | 0.02 | 0.03 | 0.08 | 0.01 | 0.37 |
| (pH 3.75) | 1 M | 0.89 | 1.87 | 0.53 | 0.12 | 0.36 | 2.04 | 6.26 |
| CC | Initial | 0.02 | 0.04 | 0.02 | 0.03 | 0.07 | 0.02 | 0.34 |
| (pH 4.0) | 1 M | 0.57 | 1.39 | 0.61 | 0.12 | 0.49 | 2.10 | 5.81 |
| CC | Initial | 0.04 | 0.10 | 0.03 | 0.07 | 0.05 | 0.02 | 0.46 |
| (pH 4.0) | 1 M | 0.71 | 1.63 | 0.54 | 0.15 | 0.44 | 2.05 | 5.99 |
| EE | Initial | 0.00 | 0.04 | 0.03 | 0.03 | 0.04 | 0.02 | 0.28 |
| (pH 5.10) | 1 M | 0.14 | 0.32 | 1.69 | 0.46 | 1.07 | 1.28 | 5.57 |

TABLE 9b-continued pH variation with Stabilizer/Tonicity Agent at 25° C./60% RH

| Formulation (pH) | Time Point | RRT 0.49 | [12-20]-BVN | [3-20]-BVN | $Asp^9$-BVN | [9-10]-BVN | [11-12]-BVN | Total |
|---|---|---|---|---|---|---|---|---|
| HH (pH 5.25) | Initial | 0.00 | 0.03 | 0.03 | 0.03 | 0.05 | 0.02 | 0.31 |
|  | 1 M | 0.16 | 0.28 | 1.81 | 0.61 | 1.21 | 1.15 | 5.90 |
| MM (pH 5.75) | Initial | 0.00 | 0.04 | 0.04 | 0.03 | 0.09 | 0.01 | 0.34 |
|  | 1 M | 0.21 | 0.11 | 2.15 | 2.11 | 1.97 | 0.52 | 7.90 |

As can be seen from the data in Tables 9a and 9b, the compositions having pH in these ranges with a suitable tonicity agent and/stabilizer provide an acceptable environment to stabilize liquid bivalirudin formulations.

Example 10: 10 mM Glycine Formulations at pH 3.0 to 3.5

Data presented in Tables 10a and 10b shows an investigation into the influence of a lower concentration of glycine (10 mM glycine) on the stability (5° C. for 3-,6-, or 12-months, and 1 month at 25° C./60% RH, respectively) of various bivalirudin formulations in the about 3.0 to about 3.5 pH range. The initial values are reported first in each data cell of Tables 10a and 10b, and the following values were from the other time points.

TABLE 10a 10 mM Glycine at pH 3.0 and 3.5, with 0.9% NaCl at 5° C.

| Formulation (pH) | Time Point | RRT 0.49 | [12-20]-BVN | [3-20]-BVN | $Asp^9$-BVN | [9-10]-BVN | [11-12]-BVN | Total |
|---|---|---|---|---|---|---|---|---|
| E (pH 3.0) | Initial | 0.01 | 0.04 | 0.01 | 0.02 | 0.05 | 0.01 | 0.23 |
|  | 3 M | 0.43 | 0.65 | 0.04 | 0.14 | 0.10 | 0.27 | 1.78 |
| N (pH 3.5) | Initial | 0.01 | 0.04 | 0.01 | 0.02 | 0.05 | 0.02 | 0.25 |
|  | 6 M | 0.58 | 1.00 | 0.13 | 0.09 | 0.22 | 0.91 | 3.20 |
|  | 12 M | 1.18 | 2.22 | 0.26 | 0.23 | 0.28 | 1.91 | 6.48 |

TABLE 10b 10 mM Glycine at pH 3.0 and 3.5, with 0.9% NaCl at 25° C./60% RH

| Formulation (pH) | Time Point | RRT 0.49 | [12-20]-BVN | [3-20]-BVN | $Asp^9$-BVN | [9-10]-BVN | [11-12]-BVN | Total |
|---|---|---|---|---|---|---|---|---|
| E (pH 3.0) | Initial | 0.01 | 0.04 | 0.01 | 0.02 | 0.05 | 0.01 | 0.23 |
|  | 1 M | 1.72 | 2.80 | 0.24 | 0.48 | 0.20 | 0.91 | 7.01 |
| N (pH 3.5) | Initial | 0.01 | 0.04 | 0.01 | 0.02 | 0.05 | 0.02 | 0.25 |
|  | 1 M | 1.32 | 2.31 | 0.38 | 0.17 | 0.29 | 1.63 | 6.52 |

As can be seen from the data in Tables 10a and 10b, the 10 mM glycine at pH in the range of about 3.0 to less than 4.0, or about 3.25 to about 3.5 provides an acceptable environment to effectively stabilize liquid bivalirudin formulations.

Example 11: Stabilizer Variation at about pH 3.5

Data presented in Tables 11a and 11b shows an investigation into the influence of stabilizer on the stability (5° C. for various months, and 1 month at 25° C./60% RH, respectively) of various bivalirudin formulations with 10 mM or 50 mM glycine in the about 3.5 to about 3.6 pH range. The initial (t=0) values are reported first in each data cell of Tables 11a and 11b, and the values following the initial value were from data points taken at various time points as indicated in the next row.

TABLE 11a

Stabilizer Variation at about pH 3.5 at 5° C.

| Formulation (pH) | Time Point | RRT 0.49 | [12-20]-BVN | [3-20]-BVN | $Asp^9$-BVN | [9-10]-BVN | [11-12]-BVN | Total |
|---|---|---|---|---|---|---|---|---|
| O (pH 3.5) | Initial | 0.01 | 0.04 | 0.01 | 0.02 | 0.05 | 0.02 | 0.24 |
|  | 3 M | 0.27 | 0.49 | 0.06 | 0.04 | 0.07 | 0.51 | 1.56 |
|  | 6 M | 0.53 | 0.96 | 0.14 | 0.08 | 0.20 | 0.97 | 3.19 |
| R (pH 3.5) | Initial | 0.01 | 0.05 | 0.02 | 0.03 | 0.07 | 0.01 | 0.31 |
|  | 6 M | 0.05 | 0.43 | 0.13 | 0.09 | 0.12 | 0.91 | 3.71 |
| T (pH 3.5) | Initial | 0.05 | 0.13 | 0.02 | 0.04 | 0.06 | 0.12 | 0.57 |
|  | 3 M | 0.25 | 0.45 | 0.09 | 0.07 | 0.09 | 0.52 | 1.66 |
|  | 6 M | 0.22 | 0.01 | 0.15 | 0.08 | 0.13 | 0.88 | 2.41 |
|  | 9 M | 0.69 | 1.25 | 0.23 | 0.10 | 0.19 | 1.42 | 4.21 |
| U (pH 3.5) | Initial | 0.05 | 0.12 | 0.03 | 0.04 | 0.05 | 0.12 | 0.68 |
|  | 3 M | 0.21 | 0.39 | 0.09 | 0.06 | 0.07 | 0.47 | 1.55 |
|  | 4 M | 0.26 | 0.50 | 0.09 | 0.06 | 0.08 | 0.60 | 2.09 |
|  | 6 M | 0.15 | 0.66 | 0.13 | 0.07 | 0.10 | 0.79 | 2.69 |
|  | 9 M | 0.00 | 0.95 | 0.20 | 0.10 | 0.12 | 1.28 | 4.48 |
| W (pH 3.5) | Initial | 0.02 | 0.06 | 0.01 | 0.03 | 0.05 | 0.02 | 0.33 |
|  | 3 M | 0.30 | 0.52 | 0.10 | 0.07 | 0.09 | 0.55 | 2.05 |
|  | 5 M 21 days | 0.47 | 0.82 | 0.13 | 0.07 | 0.11 | 0.89 | 2.72 |
|  | 9 M | 0.76 | 1.47 | 0.23 | 0.18 | 0.21 | 1.54 | 4.69 |
|  | 12 M | 0.85 | 1.46 | 0.26 | 0.14 | 0.20 | 0.79 | 4.09 |
|  | 15 M | 1.26 | 2.18 | 0.36 | 0.16 | 0.31 | 2.25 | 7.06 |
|  | 18 M | 0.08 | 2.76 | 0.47 | 0.17 | 0.37 | 2.72 | 8.68 |

TABLE 11a-continued

Stabilizer Variation at about pH 3.5 at 5° C.

| Formulation (pH) | Time Point | RRT 0.49 | [12-20]-BVN | [3-20]-BVN | Asp⁹-BVN | [9-10]-BVN | [11-12]-BVN | Total |
|---|---|---|---|---|---|---|---|---|
| Y (pH 3.6) | Initial | 0.03 | 0.07 | 0.04 | 0.05 | 0.09 | 0.04 | 0.45 |
| | 3 M | 0.22 | 0.47 | 0.11 | 0.11 | 0.11 | 0.63 | 1.83 |
| AA (pH 3.6) | Initial | 0.00 | 0.04 | 0.02 | 0.05 | 0.12 | 0.01 | 0.36 |
| | 3 M | 0.20 | 0.44 | 0.07 | 0.10 | 0.11 | 0.55 | 1.67 |
| | 5 M 08 days | 0.02 | 0.66 | 0.14 | 0.08 | 0.13 | 0.84 | 2.43 |
| | 9 M | 0.66 | 1.19 | 0.24 | 0.11 | 0.22 | 1.45 | 4.17 |
| | 12 M | 0.01 | 1.65 | 0.34 | 0.12 | 0.23 | 1.93 | 5.52 |

TABLE 11b

Stabilizer Variation at about pH 3.5 at 25° C./60% RH

| Formulation (pH) | Time Point | RRT 0.49 | [12-20]-BVN | [3-20]-BVN | Asp⁹-BVN | [9-10]-BVN | [11-12]-BVN | Total |
|---|---|---|---|---|---|---|---|---|
| O (pH 3.5) | Initial | 0.01 | 0.04 | 0.01 | 0.02 | 0.05 | 0.02 | 0.24 |
| | 1 M | 1.14 | 2.12 | 0.40 | 0.16 | 0.22 | 1.66 | 6.23 |
| R (pH 3.5) | Initial | 0.01 | 0.05 | 0.02 | 0.03 | 0.07 | 0.01 | 0.31 |
| | 1 M | 1.08 | 2.02 | 0.34 | 0.14 | 0.23 | 1.49 | 6.34 |
| T (pH 3.5) | Initial | 0.05 | 0.13 | 0.02 | 0.04 | 0.06 | 0.12 | 0.57 |
| | 1 M | 0.92 | 1.83 | 0.42 | 0.10 | 0.28 | 1.57 | 5.63 |
| U (pH 3.5) | Initial | 0.05 | 0.12 | 0.03 | 0.04 | 0.05 | 0.12 | 0.68 |
| | 1 M | 0.78 | 1.55 | 0.37 | 0.10 | 0.23 | 1.45 | 5.47 |
| V (pH 3.5) | Initial | 0.02 | 0.07 | 0.02 | 0.03 | 0.04 | 0.04 | 0.31 |
| | 1 M | 0.98 | 1.90 | 0.45 | 0.15 | 0.29 | 1.76 | 5.88 |
| W (pH 3.5) | Initial | 0.02 | 0.06 | 0.01 | 0.03 | 0.05 | 0.02 | 0.33 |
| | 1 M | 1.00 | 1.83 | 0.40 | 0.12 | 0.20 | 1.56 | 5.55 |
| Y (pH 3.6) | Initial | 0.03 | 0.07 | 0.04 | 0.05 | 0.09 | 0.04 | 0.45 |
| | 1 M | 0.81 | 1.64 | 0.44 | 0.10 | 0.30 | 1.80 | 5.69 |
| Z (pH 3.6) | Initial | 0.02 | 0.08 | 0.03 | 0.05 | 0.08 | 0.08 | 0.42 |
| | 1 M | 0.77 | 1.69 | 0.49 | 0.11 | 0.33 | 1.90 | 5.71 |
| AA (pH 3.6) | Initial | 0.00 | 0.04 | 0.02 | 0.05 | 0.12 | 0.01 | 0.36 |
| | 1 M | 0.76 | 1.52 | 0.43 | 0.10 | 0.27 | 1.56 | 4.97 |

As can be seen from the data in Tables 11a and 11b, the various stabilizers provide an acceptable environment to effectively stabilize liquid bivalirudin formulations in this pH range.

Example 12: Stabilizer Variation at about pH 5.25

Data presented in Tables 12a and 12 b shows an investigation into the influence of stabilizer on the stability (5° C. for various months, and 1 month at 25° C./60% RH, respectively) of various bivalirudin formulations with 6 or 28 mM buffer strength (acetate) in the pH range of about 5.25 to about 5.3. The initial values (t=0) are reported first in each data cell of Tables 12a and 12b, and the values following the initial value were from data points taken at various time points as indicated in the second column.

TABLE 12a

Stabilizer Variation at about pH 5.25 at 5° C.

| Formulation (pH) | Time Point | RRT 0.49 | [12-20]-BVN | [3-20]-BVN | Asp⁹-BVN | [9-10]-BVN | [11-12]-BVN | Total |
|---|---|---|---|---|---|---|---|---|
| HH (pH 5.25) | Initial | 0.00 | 0.03 | 0.03 | 0.03 | 0.05 | 0.02 | 0.31 |
| | 3 M | 0.02 | 0.09 | 0.41 | 0.11 | 0.44 | 0.46 | 1.88 |
| | 5 M 21 days | 0.02 | 0.16 | 0.65 | 0.19 | 0.80 | 0.76 | 2.95 |
| | 9 M | 0.05 | 0.20 | 1.07 | 0.51 | 0.92 | 1.05 | 4.21 |
| II (pH 5.25) | Initial | 0.00 | 0.04 | 0.04 | 0.04 | 0.06 | 0.02 | 0.34 |
| | 3 M | 0.02 | 0.09 | 0.39 | 0.13 | 0.48 | 0.41 | 1.79 |
| | 5 M 21 days | 0.02 | 0.14 | 0.61 | 0.23 | 0.68 | 0.62 | 2.60 |
| | 9 M | 0.07 | 0.22 | 1.06 | 0.63 | 1.00 | 0.94 | 4.26 |
| JJ (pH 5.25) | Initial | 0.01 | 0.04 | 0.04 | 0.04 | 0.06 | 0.02 | 0.33 |
| | 3 M | 0.02 | 0.09 | 0.36 | 0.13 | 0.50 | 0.40 | 1.85 |
| FF (pH 5.3) | Initial | 0.00 | 0.04 | 0.06 | 0.05 | 0.09 | 0.04 | 0.44 |
| | 3 M | 0.02 | 0.07 | 0.40 | 0.21 | 0.57 | 0.37 | 1.85 |
| GG (pH 5.3) | Initial | 0.00 | 0.05 | 0.03 | 0.06 | 0.05 | 0.02 | 0.30 |
| | 3 M | 0.00 | 0.10 | 0.37 | 0.12 | 0.46 | 0.45 | 1.61 |
| | 5 M 09 days | 0.02 | 0.13 | 0.56 | 0.19 | 0.56 | 0.63 | 2.35 |
| | 9 M | 0.02 | 0.21 | 0.95 | 0.41 | 0.81 | 0.97 | 3.82 |
| | 12 M | 0.07 | 0.28 | 1.32 | 0.61 | 0.95 | 1.24 | 4.94 |

TABLE 12b

Stabilizer Variation at about pH 5.25 at 25° C./60% RH

| Formulation (pH) | Time Point | RRT 0.49 | [12-20]-BVN | [3-20]-BVN | Asp$^9$-BVN | [9-10]-BVN | [11-12]-BVN | Total |
|---|---|---|---|---|---|---|---|---|
| HH | Initial | 0.00 | 0.03 | 0.03 | 0.03 | 0.05 | 0.02 | 0.31 |
| (pH 5.25) | 1 M | 0.16 | 0.28 | 1.81 | 0.61 | 1.21 | 1.15 | 5.90 |
| II | Initial | 0.00 | 0.04 | 0.04 | 0.04 | 0.06 | 0.02 | 0.34 |
| (pH 5.25) | 1 M | 0.16 | 0.25 | 1.80 | 0.01 | 1.30 | 1.02 | 6.02 |
| JJ | Initial | 0.01 | 0.04 | 0.04 | 0.04 | 0.06 | 0.02 | 0.33 |
| (pH 5.25) | 1 M | 0.13 | 0.26 | 1.64 | 0.72 | 1.30 | 1.00 | 5.72 |
| FF | Initial | 0.00 | 0.04 | 0.06 | 0.05 | 0.09 | 0.04 | 0.44 |
| (pH 5.3) | 1 M | 0.14 | 0.23 | 1.75 | 0.97 | 1.47 | 0.89 | 6.18 |
| GG | Initial | 0.00 | 0.05 | 0.03 | 0.06 | 0.05 | 0.02 | 0.30 |
| (pH 5.3) | 1 M | 0.02 | 0.26 | 1.78 | 0.54 | 1.14 | 1.16 | 5.77 |

As can be seen from the data in Tables 12a and 12b, the various stabilizers provide an acceptable environment to effectively stabilize liquid bivalirudin formulations in this pH range.

Example 13: Amino Acids as Stabilizers/Tonicity Agents

Data presented in Tables 13a and 13b shows an investigation into the influence of amino acids on the stability (5° C. for various months, and 1 month at 25° C./60% RH, respectively) of various bivalirudin formulations with 50 or 300 mM glycine, in the pH range of about 3.5 to about 3.8. The initial values (t=0) are reported first in each data cell of Tables 13a and 13b, and the values following the initial value were from data points taken at various time points as indicated in the second column.

TABLE 13a

Stability at 5° C.-Amino Acid Variation

| Formulation (pH) | Time Point | RRT 0.49 | [12-20]-BVN | [3-20]-BVN | Asp$^9$-BVN | [9-10]-BVN | [11-12]-BVN | Total |
|---|---|---|---|---|---|---|---|---|
| S1 | Initial | 0.01 | 0.04 | 0.02 | 0.03 | 0.07 | 0.01 | 0.27 |
| (pH 3.5) | 3 M | 0.37 | 0.66 | 0.09 | 0.07 | 0.09 | 0.59 | 2.07 |
| S2 | Initial | 0.02 | 0.06 | 0.02 | 0.04 | 0.05 | 0.02 | 0.32 |
| (pH 3.5) | 3 M | 0.29 | 0.52 | 0.12 | 0.07 | 0.10 | 0.59 | 1.92 |
|  | 5 M 21 days | 0.55 | 0.93 | 0.16 | 0.08 | 0.15 | 1.09 | 3.18 |
|  | 9 M | 1.03 | 1.72 | 0.26 | 0.18 | 0.25 | 1.78 | 6.17 |
| V | Initial | 0.02 | 0.07 | 0.02 | 0.03 | 0.04 | 0.04 | 0.31 |
| (pH 3.5) | 3 M | 0.29 | 0.58 | 0.12 | 0.08 | 0.10 | 0.62 | 1.95 |
|  | 5 M 21 days | 0.55 | 1.04 | 0.15 | 0.05 | 0.12 | 1.14 | 3.25 |
|  | 9 M | 0.76 | 1.54 | 0.26 | 0.18 | 0.24 | 1.75 | 5.03 |
| Z | Initial | 0.02 | 0.08 | 0.03 | 0.05 | 0.08 | 0.08 | 0.42 |
| (pH 3.6) | 3 M | 0.20 | 0.50 | 0.12 | 0.09 | 0.11 | 0.67 | 1.81 |
| OO | Initial | 0.01 | 0.05 | 0.02 | 0.03 | 0.05 | 0.02 | 0.27 |
| (pH 3.8) | 3 M | 0.17 | 0.48 | 0.13 | 0.06 | 0.12 | 0.69 | 1.80 |
|  | 5 M 21 days | 0.33 | 0.74 | 0.19 | 0.06 | 0.22 | 1.17 | 3.01 |
|  | 9 M | 0.51 | 1.22 | 0.32 | 0.14 | 0.13 | 1.86 | 4.41 |

TABLE 13b

Stability at 25° C./60% RH-Amino Acid Variation

| Formulation (pH) | Time Point | RRT 0.49 | [12-20]-BVN | [3-20]-BVN | Asp$^9$-BVN | [9-10]-BVN | [11-12]-BVN | Total |
|---|---|---|---|---|---|---|---|---|
| S1 | Initial | 0.01 | 0.04 | 0.02 | 0.03 | 0.07 | 0.01 | 0.27 |
| (pH 3.5) | 1 M | 0.97 | 1.96 | 0.44 | 0.13 | 0.31 | 1.80 | 5.96 |
| S2 | Initial | 0.02 | 0.06 | 0.02 | 0.04 | 0.05 | 0.02 | 0.32 |
| (pH 3.5) | 1 M | 1.12 | 1.96 | 0.45 | 0.15 | 0.29 | 1.79 | 6.13 |
| V | Initial | 0.02 | 0.07 | 0.02 | 0.03 | 0.04 | 0.04 | 0.31 |
| (pH 3.5) | 1 M | 0.98 | 1.90 | 0.45 | 0.15 | 0.29 | 1.76 | 5.88 |

TABLE 13b-continued

Stability at 25° C./60% RH-Amino Acid Variation

| Formulation (pH) | Time Point | RRT 0.49 | [12-20]-BVN | [3-20]-BVN | Asp$^9$-BVN | [9-10]-BVN | [11-12]-BVN | Total |
|---|---|---|---|---|---|---|---|---|
| Z | Initial | 0.02 | 0.08 | 0.03 | 0.05 | 0.08 | 0.08 | 0.42 |
| (pH 3.6) | 1 M | 0.77 | 1.69 | 0.49 | 0.11 | 0.33 | 1.90 | 5.71 |
| AA | Initial | 0.00 | 0.04 | 0.02 | 0.05 | 0.12 | 0.01 | 0.36 |
| (pH 3.6) | 1 M | 0.76 | 1.52 | 0.43 | 0.10 | 0.27 | 1.56 | 4.97 |
| OO | Initial | 0.01 | 0.05 | 0.02 | 0.03 | 0.05 | 0.02 | 0.27 |
| (pH 3.8) | 1 M | 0.60 | 1.51 | 0.55 | 0.11 | 0.35 | 1.96 | 5.56 |

As can be seen from the data in Tables 13a and 13b, the various amino acids provide an acceptable environment to effectively stabilize liquid bivalirudin formulations in this pH range.

Example 14: Long Term Stability Data, Specific Embodiments

Table 14a provides data for long term stability (5° C.) of preferred embodiments of this invention for up to 18 months, and Table 14b provides stability data after 1 month at 25° C./60% RH. In all cases, the impurity profile after 1 month under accelerated conditions is predictive of the long-term data at the 12-month time point.

TABLE 14a

Long Term Stability Data for Exemplified Embodiments of the Present Disclosure

| Formulation (pH) | Time Point | RRT 0.49 | [12-20]-BVN | [3-20]-BVN | Asp$^9$-BVN | [9-10]-BVN | [11-12]-BVN | Total |
|---|---|---|---|---|---|---|---|---|
| X | Initial | 0.03 | 0.09 | 0.02 | 0.07 | 0.06 | 0.05 | 0.43 |
| (pH 3.5) | 3 M (U) | 0.28 | 0.54 | 0.11 | 0.08 | 0.10 | 0.61 | 1.80 |
| | 6 M (U) | 0.47 | 0.87 | 0.18 | 0.09 | 0.15 | 1.02 | 3.04 |
| | 9 M (U) | 0.03 | 1.37 | 0.26 | 0.10 | 0.22 | 1.58 | 4.62 |
| | 12 M (U) | 0.06 | 1.84 | 0.34 | 0.15 | 0.30 | 2.05 | 6.26 |
| | 3 M (I) | 0.27 | 0.52 | 0.11 | 0.07 | 0.09 | 0.60 | 1.75 |
| | 6 M (I) | 0.47 | 0.90 | 0.18 | 0.09 | 0.15 | 1.04 | 3.10 |
| | 9 M (I) | 0.03 | 1.37 | 0.25 | 0.10 | 0.21 | 1.57 | 4.61 |
| | 12 M (I) | 0.06 | 1.82 | 0.34 | 0.15 | 0.29 | 2.04 | 6.24 |
| AA | Initial | 0.00 | 0.04 | 0.02 | 0.05 | 0.12 | 0.01 | 0.36 |
| (pH 3.6) | 3 M | 0.20 | 0.44 | 0.07 | 0.10 | 0.11 | 0.55 | 1.67 |
| | 5 M 08 days | 0.02 | 0.66 | 0.14 | 0.08 | 0.13 | 0.84 | 2.43 |
| | 9 M | 0.66 | 1.19 | 0.24 | 0.11 | 0.22 | 1.45 | 4.17 |
| KK | 12 M | 0.01 | 1.65 | 0.34 | 0.12 | 0.23 | 1.93 | 5.52 |
| (pH 5.25) | Initial | 0.00 | 0.05 | 0.02 | 0.04 | 0.05 | 0.01 | 0.27 |
| | 3 M (U) | 0.01 | 0.12 | 0.43 | 0.12 | 0.41 | 0.50 | 1.71 |
| | 6 M (U) | 0.00 | 0.17 | 0.70 | 0.24 | 0.63 | 0.77 | 2.80 |
| | 9 M (U) | 0.04 | 0.24 | 1.06 | 0.44 | 0.85 | 1.08 | 4.12 |
| | 12 M (U) | 0.11 | 0.32 | 1.40 | 0.70 | 1.03 | 1.26 | 5.33 |
| | 15 M (U) | 0.11 | 0.34 | 1.55 | 0.79 | 1.08 | 1.35 | 5.81 |
| | 18 M (U) | 0.13 | 0.41 | 1.77 | 1.05 | 1.11 | 1.46 | 6.52 |
| | 3 M (I) | 0.01 | 0.12 | 0.42 | 0.12 | 0.37 | 0.49 | 1.63 |
| | 6 M (I) | 0.00 | 0.17 | 0.70 | 0.24 | 0.63 | 0.77 | 2.80 |
| | 9 M (I) | 0.03 | 0.24 | 1.07 | 0.44 | 0.85 | 1.08 | 4.14 |
| | 12 M (I) | 0.11 | 0.32 | 1.38 | 0.68 | 1.02 | 1.26 | 5.28 |
| | 15 M (I) | 0.11 | 0.34 | 1.54 | 0.79 | 1.06 | 1.46 | 5.77 |
| | 18 M (I) | 0.13 | 0.41 | 1.77 | 1.05 | 1.10 | 1.46 | 6.51 |
| GG | Initial | 0.00 | 0.05 | 0.03 | 0.06 | 0.05 | 0.02 | 0.30 |
| (pH 5.3) | 3 M | 0.00 | 0.10 | 0.37 | 0.12 | 0.46 | 0.45 | 1.61 |
| | 5 M 09 days | 0.02 | 0.13 | 0.56 | 0.19 | 0.56 | 0.63 | 2.35 |
| | 9 M | 0.02 | 0.21 | 0.95 | 0.41 | 0.81 | 0.97 | 3.82 |
| | 12 M | 0.07 | 0.28 | 1.32 | 0.61 | 0.95 | 1.24 | 4.94 |

TABLE 14b

25C Stability Data for Exemplified Embodiments of the Present Disclosure

| Formulation (pH) | Time Point | RRT 0.49 | [12-20]-BVN | [3-20]-BVN | Asp$^9$-BVN | [9-10]-BVN | [11-12]-BVN | Total |
|---|---|---|---|---|---|---|---|---|
| X | Initial | 0.03 | 0.09 | 0.02 | 0.07 | 0.06 | 0.05 | 0.43 |
| (pH 3.5) | 1 M (U) | 0.97 | 1.83 | 0.47 | 0.13 | 0.30 | 1.72 | 5.93 |
| | 1 M (I) | 0.98 | 1.82 | 0.46 | 0.13 | 0.30 | 1.72 | 5.93 |
| AA | Initial | 0.00 | 0.04 | 0.02 | 0.05 | 0.12 | 0.01 | 0.36 |
| (pH 3.6) | 1 M | 0.76 | 1.52 | 0.43 | 0.10 | 0.27 | 1.56 | 4.97 |
| KK | Initial | 0.00 | 0.05 | 0.02 | 0.04 | 0.05 | 0.01 | 0.27 |
| (pH 5.25) | 1 M (U) | 0.03 | 0.30 | 1.90 | 0.62 | 1.18 | 1.21 | 6.11 |
| | 1 M (I) | 0.03 | 0.32 | 1.99 | 0.65 | 1.23 | 1.26 | 6.36 |
| GG | Initial | 0.00 | 0.05 | 0.03 | 0.06 | 0.05 | 0.02 | 0.30 |
| (pH 5.3) | 1 M | 0.02 | 0.26 | 1.78 | 0.54 | 1.14 | 1.16 | 5.77 |

Example 15: Hemolysis Study

Hemolysis studies were performed on Formulation KK to demonstrate that there is no incompatibility with whole human blood for the bivalirudin products described herein. The relevant details of this investigation are provided in Table 15a.

TABLE 15a

Hemolysis Study Design

| Study Parameter | Hemolysis Study |
|---|---|
| Test Matrix | Whole human blood with K$_2$EDTA as anticoagulant |
| Test Concentration | 2.14 mg/mL (Blood:Drug Ratio = 1:0.75) |
| Incubation Conditions | 37 ± 5° C. for 30 minutes |
| Centrifugation Conditions (to separate plasma after incubation) | 2570 g for 5 minutes at ambient temperature |
| No. of Replicates | 3 |
| Test Drug | Bivalirudin Injection, 5 mg/mL |
| Test Item Vehicle | Bivalirudin Injection Placebo |
| Reference Drug | Angiomax (bivalirudin) for Injection |

TABLE 15a-continued

Hemolysis Study Design

| Study Parameter | Hemolysis Study |
|---|---|
| Negative Control | 0.9% NaCl control or Whole blood control |
| Positive Control | 1% Saponin |
| Measurement | Direct measurement of hemoglobin using an Advia 120 hematology(Hb) analyzer (cyanmethemoglobin method) |
| % Hemolysis Determination | Based on Hb content of the sample as a percent of the Hb content of the donor, after adjusting for dilution and interference from the sample (if any) |

Briefly, human whole blood was collected from a single donor (K2EDTA anticoagulant). The donor blood was analyzed for hemoglobin content in triplicate using an Advia 120 hematology analyzer. The dynamic mixing of drug infusate in human whole blood was simulated in this in vitro study by incubating the diluted test, reference and placebo items at a blood:formulation ratio of 1:0.75, corresponding to a final bivalirudin concentration of 2.14 mg/mL. Blood was mixed with either bivalirudin for injection as described herein, Angiomax®, a bivalirudin placebo, or 0.9% saline. The mixture as incubated at 37° C. (±5° C.) for 30 minutes. Negative controls containing only blood (whole blood control) or blood mixed with 0.9% saline at a blood:saline ratio of 1:0.75 (0.9% NaCl control) were also prepared. A positive control containing blood mixed 1:1 with 1% saponin was also prepared. All control tubes were incubated at 37° C. (±5° C.) for 30 minutes. Each sample was tested in triplicate. During the incubation tubes containing the test and reference item mixed with saline were prepared to check if the test or reference item interfered with the absorbance readings. After incubation, the blood and saline tubes were centrifuged at 2570 g for 5 minutes at ambient temperature. The supernatant was tested for hemoglobin on the Advia® 120. The percent hemolysis of each sample was calculated based on the hemoglobin content of the supernatant, expressed as a percentage of hemoglobin content of the donor sample, after correcting for dilution and interference from the sample, if any.

The following acceptance criteria were used for the study: the 1% Saponin positive control must demonstrate a % hemolysis value of >25% for the assay run to be considered acceptable; and the two negative controls for hemolysis must demonstrate a % hemolysis value of <10% for the assay run to be considered acceptable.

The following criteria were used to assess hemolytic potential: a treated sample must demonstrate a percent hemolysis value of >25% to be definitive as positive for hemolysis; a treated sample must demonstrate a percent hemolysis value of <10% to be definitive as negative for hemolysis; and a treated sample that demonstrates a percent hemolysis value of >10% and <25% will be considered indicative, but not definitive of hemolysis.

The results of the hemolysis study, summarized in Table 15b, showed that no hemoglobin, and therefore no hemolysis (0% hemolysis), was detected in samples which had been treated with Formulation KK (pH 5.5, 10 mM acetate buffer, with 10% PEG 400) described herein, the reference listed drug, or the negative controls. Hemoglobin was successfully detected in samples which had been treated with positive control (saponin, 100% hemolysis). The positive control for hemolysis demonstrated a % hemolysis value of >25%, the two negative controls demonstrated a % hemolysis value of <10% and therefore the assay run was considered acceptable.

TABLE 15b

Summary of Hemolysis Study Results

| Treatment | Corrected Hemoglobin Concentration (g/dL)* | % Hemolysis* |
|---|---|---|
| Bivalirudin Injection as described herein | 0.0 ± 0.0 | 0.0 ± 0.0 |
| Angiomax (bivalirudin) for Injection | 0.0 ± 0.0 | 0.0 ± 0.0 |
| Bivalirudin Injection Placebo as described herein | 0.0 ± 0.0 | 0.0 ± 0.0 |
| Negative Control (0.9% Saline) | 0.0 ± 0.0 | 0.0 ± 0.0 |
| Negative Control (whole blood only) | 0.0 ± 0.0 | 0.0 ± 0.0 |
| Positive Control (1% saponin) | 7.47 ± 0.06 | 100.0 ± 0.8 |

*Based on average (and standard deviation) of three replicates

The samples treated with Bivalirudin Injection as described herein, Angiomax®, or the Bivalirudin Injection Placebo as described herein all had % hemolysis values of <10% and were therefore considered to be definitively negative for hemolysis.

Example 16: Continuous Infusion Repeat Dose Rat Toxicology Study

The safety of the degradants (impurities) disclosed in the formulation of the present invention was established in a GLP-compliant 14-day continuous infusion repeat-dose toxicity study in rats. The 14-day repeat-dose toxicity study compared the toxicity of an intentionally degraded exemplary formulation of this invention (Test Article) to the marketed authorized generic for Angiomax for Injection (Reference Article)—note that the authorized generic is the same product as Angiomax but marketed under a different label (in this case Sandoz). In this study, a batch of formulation KK was intentionally heat-degraded at 40° C. for 14 days to contain about 19% total impurities and then continuously intravenously infused 24 hours per day for 14 consecutive days at dosages of 36, 100 and approximately 258 mg/kg/day (maximum feasible dose), containing 6.8 mg/kg/day, 19 mg/kg/day, and 49 mg/kg/day of impurities, respectively. The authorized generic for Angiomax was administered similarly at 258 mg/kg/day, which contained a dose of less than 2 mg/kg/day of impurities. Table 16a summarizes the degradant levels of the Test and Reference Articles used in the study; the Test Article was tested on Days 1, 7, and 15 of the study, while the Reference Article was tested immediately and 48 hours after reconstitution and dilution.

TABLE 16a

Analytical Characterization of Test and Reference Articles used in the Toxicology Study

| Impurity Attribute | Test Drug (Formulation KK intentionally degraded at 40° C. for 14 days) | | | Reference Drug (Authorized generic of Angiomax for Injection, Lot 00117), after reconstitution | |
|---|---|---|---|---|---|
| | Day 1 | Day 7 | Day 15 | Initial | 48 hours after reconstitution |
| RRT 0.49 | 1.6% | 1.7% | 1.8% | Not detected | Not detected |
| [12-20]- | 1.0% | 1.0% | 0.95% | 0.08% | 0.09% |

TABLE 16a-continued

Analytical Characterization of Test and Reference Articles used in the Toxicology Study

| | Test Drug (Formulation KK intentionally degraded at 40° C. for 14 days) | | | Reference Drug (Authorized generic of Angiomax for Injection, Lot 00117), after reconstitution | |
|---|---|---|---|---|---|
| Impurity Attribute | Day 1 | Day 7 | Day 15 | Initial | 48 hours after reconstitution |
| bivalirudin [3-20]- | 5.9% | 6.0% | 6.1% | 0.12% | 0.21% |
| bivalirudin [Asp$^9$]- | 2.4% | 2.5% | 2.6% | 0.14% | 0.16% |
| bivalirudin [9-10]-cycloimido | 2.5% | 2.5% | 2.5% | 0.06% | 0.18% |
| bivalirudin [11-12]-cycloimido | 2.6% | 2.6% | 2.6% | 0.10% | 0.11% |
| Total Impurities | 18.7% | 19.1% | 19.1% | 0.60% | 0.77% |

In the study, Sprague-Dawley rats (10/sex/group) were continuously intravenously infused for 24 hours a day for 14 consecutive days (Days 1-14) with placebo (0.9% sodium chloride), Test Article vehicle (0.8 mg/mL sodium acetate trihydrate and 100 mg/mL polyethylene glycol 400, pH 5.25), Reference Article at approximately 258 mg/kg/day or Test Article at 36, 100 and approximately 258 mg/kg/day. The infusion rate was 2.5 mL/kg/h for all groups. A separate set of satellite animals (6/sex/group) were administered the same set of materials and used for evaluating the toxicokinetics (TK) of bivalirudin at 5 minutes and 24 hours after termination of dosing (3 animals/sex/group/timepoint). See Table 16b for group allocation. All animals were sacrificed on Day 16, one day following the end of the 14-day infusion.

TABLE 16b

Group Allocations of Toxicology Study

| | | No. of Toxicity Animals | | No. of Toxico-kinetic Animals | | Bivalirudin Dose | Concentration | Degradant dose |
|---|---|---|---|---|---|---|---|---|
| Group | Treatment | M | F | M | F | (mg/kg/day) | (mg/mL) | (mg/kg/day) |
| 1 | Placebo-0.9% sodium chloride | 10 | 10 | 6 | 6 | 0 | 0 | 0 |
| 2 | Test Article Vehicle | 10 | 10 | 6 | 6 | 0 | 0 | 0 |
| 3 | Test Article | 10 | 10 | 6 | 6 | 36 | 0.6 | 6.8 |
| 4 | Test Article | 10 | 10 | 6 | 6 | 100 | 1.37 | 19 |
| 5 | Test Article | 10 | 10 | 6 | 6 | ~258 | ~4.3 | 49 |
| 6 | Comparator-Reference Article | 10 | 10 | 6 | 6 | ~258 | ~4.3 | <2 |

Results
Mortalities

A total of seven animals, three Toxicity animals that were treated with bivalirudin and three TK animals, were sacrificed moribund or found dead during the study. With respect to the bivalirudin-treated Toxicity animals, the premature sacrifices of these animals, two high-dose (258 mg/kg/day) Test Article-treated males and one high-dose Reference Article-treated male, were attributed to the pharmacology of bivalirudin. These animals displayed abnormal clinical signs consisting of decreased activity, hunched posture, abnormal color or pallor, piloerection, cold to touch, and/or irregular breathing prior to their sacrifice. In these three high-dose (258 mg/kg/day) early decedents, the dark material in the gastrointestinal tract and hemoglobin crystals in the lung was consistent with hemorrhage, and the pallor of the skin and organs was considered to be due to blood loss. These findings were considered associated with the mode of action of bivalirudin (direct-acting thrombin inhibitor).

With respect to the TK animals, two Test Article-treated animals (one mid-dose and one high dose) and one high-dose Reference Article-treated animal were found dead or sacrificed. All three animals had thin red fluid within the abdominal cavity; these gross findings are often seen in unscheduled decedents and therefore could not be attributed definitively to the mode of action of bivalirudin (histopathology was not performed).

Findings in Surviving Animals

In the animals that survived until the end of the study, there were no test article-related effects on clinical observations, body weights, food consumption, hematology, coagulation, urinalysis or organ weights. The only clinical chemistry findings were an approximate 20-30% decrease in glucose in both high-dose group male animals (groups 5 and 6), compared to control, at the end of dosing on Day 15. These decreases were considered non-adverse due to their relatively small magnitude.

Macroscopically, a single Test Article-treated high-dose female had unilateral red ovarian cyst, correlating microscopically with hemorrhage and fibrin deposition within a corpora luteum. These effects were considered a consequence of the biological activity of bivalirudin.

Procedure-related macroscopic and microscopic findings associated with catheter placement and maintenance were present at the infusion site in both control and treated groups at similar severity and frequency; these findings consisted of vascular changes of intimal proliferation/fibrosis, thrombus formation, and/or inflammatory cell infiltrates. Finally, 1 female in the low-dose (36 mg/kg/day) Test Article treated animal had bacterial infection of the catheter site with systemic spread to lungs, kidneys and skeletal muscle. These findings were consistent with prolonged catheter placement and are known effects and complications of infusion studies in rodents.

Toxicokinetics

In the surviving TK animals, plasma concentrations of bivalirudin were quantifiable at the first sampling time (5 minutes post-dose on Day 15) for all test article-treated animals except for one high-dose (258 mg/kg/day) Reference Article-treated female. It is noted that this animal was found to have leaking or disconnected infusion line on two occasions (observed between Day 8-9 and between Day 12-13), but the test article was presumably administered from Day 13-15 and therefore the cause of the no exposure is unknown. At the 24-hour timepoint only 7 out of 23 samples (range 50.5-159 ng/mL) had bivalirudin concentrations, all other samples were below the lower level of quantitation (50 ng/mL). These results are consistent with the expected short half-life of bivalirudin.

Mean plasma concentrations of bivalirudin at 5 minutes post-dose (C5) increased approximately proportionately with increasing dose over the dose range 36 to ~258 mg/kg/day on Day 15 (after termination of dosing) (Table 16c). Mean plasma concentrations of bivalirudin at C5 were similar in males treated with the high-dose (250 mg/kg/day) of MAIA Bivalirudin Injection or Sandoz Bivalirudin, and only slightly lower (approximately 20% lower) in the female treated with MAIA Bivalirudin than in the females treated with Sandoz Bivalirudin. However, it must be noted that data are available from just one female for the MAIA product, due to premature deaths or inability to collect blood.

TABLE 16c

Plasma Concentrations of Bivalirudin ($C_5$) Five Minutes Following End of Infusion

| Bivalirudin dose level (mg/kg/day) | $C_5$ (ng/mL) Day 15 Males | $C_5$ (ng/mL) Day 15 Females | $C_5$/D [(ng/ml)/(mg/kg)] Day 15 Males | $C_5$/D [(ng/ml)/(mg/kg)] Day 15 Females |
| --- | --- | --- | --- | --- |
| 36 (Test Article) | 961 ± 283 | 593 ± 88 | 26.7 | 16.5 |
| 100 (Test Article) | 2500 ± 200 | 1800 ± 300 | 25.0 | 18.0 |
| ~258 (Test Article)[a] | 7240 ± 120 | 5360* | 28.1 | 20.8* |
| ~258 (Reference Article)[b] | 7270** | 6700** | 28.2** | 26.0** |

*based on one animal,
**based on two animals,
[a]One high-dose female was found dead prior to study termination and no sample could be collected from a second high-dose female animal despite several attempts.
[b]One high-dose male animal was sacrificed moribund prior to the end of dosing; data from female Animal 6633 was not included in the mean as the value was considered an outlier.

CONCLUSION

A 14-day infusion of the Test Article up to 100 mg/kg/day was tolerated with no test article effects observed. At the highest dose (258 mg/kg/day), the Test Article and Reference Article caused mortality that was related directly or indirectly to hemorrhage, which is consistent with the pharmacology of the product. The effects consisted of dark material in the gastrointestinal tract, pallor of the skin and organs, centrilobular necrosis in the liver and hemoglobin crystals in the lungs. Hemorrhage was also observed in the ovary in a 258 mg/kg/day female given Test Article that survived to study termination. In high-dose (258 mg/kg/day) animals that survived until the end of the study, only a minor, non-adverse decrease in glucose was observed in males with both the Test and Reference Articles. Due to the test article-related premature deaths, the NOAEL of the Test Article was determined to be 100 mg/kg/day, which corresponds with a Cmax of 2500±200 ng/ml in males and 1800±300 ng/mL in females. Overall, there were no differences noted between rats administered the Test Article and rats administered the Reference Article. Additionally, degradant impurities of the Test Article (19%) up to an impurity dose of 49 mg/kg/day intravenously infused for 14 continuous days did not induce any unexpected toxicities, thereby qualifying their safety.

Example 17: In-Vitro Pharmacodynamic Study

An in-vitro study was performed to compare the (pharmacodynamic) effects of an exemplary ready-to-use liquid formulation of this disclosure (Formulation KK) at the end of its shelf-life and the Angiomax (bivalirudin) for Injection, 250 mg/vial) on the (i) Prothrombin Time (PT) assay, (ii) the activated Partial Thromboplastin Time (aPTT) assay and (iii) the Thrombin Time (TT) assay over the therapeutic concentration range in male and female plasma samples. The purpose of the study was to demonstrate that the degradant levels found in exemplary formulations of this invention do not adversely affect the efficacy of bivalirudin in terms of its anticoagulant (pharmacodynamic) activity.

In this study, a batch of formulation KK was intentionally heat-degraded at 30° C. for 10 days to contain about 7% total impurities (Test Drug) and compared against Angiomax for Injection (Reference Drug) for PT, aPTT,a and TT in human plasma. Table 17a summarizes the impurity levels in the Test and Reference Drug used in the study.

TABLE 17a

Impurity Profile of Test and Reference Drug used in the Pharmacodynamic Study

| Attribute | Test Drug (Formulation KK, 30 ± 2° C. for 10 days) | Reference Drug (Angiomax for Injection, Lot 00111)‡ |
| --- | --- | --- |
| RRT 0.49 | 0.30% | 0.09% |
| [12-20]-bivalirudin | 0.42% | 0.15% |
| [3-20]-bivalirudin | 2.17% | 0.09% |
| [Asp$^9$]-bivalirudin | 0.94% | 0.23% |
| [9-10]-cycloimido bivalirudin | 1.17% | Not detected |
| [11-12]-cycloimido bivalirudin | 1.64% | 0.03% |
| Total Impurities | 7.22% | 0.70% |

This study employed a design that is similar to an open controlled 2-way replicated crossover study that is traditionally used for the assessment of bioequivalence between a Test Drug and a Reference Drug; the study parameters are summarized in Table 17b.

TABLE 17b

Pharmacodynamic Study Parameters

| Study Parameter | Pivotal Study (MAIA-BVN-CLOT-003) |
| --- | --- |
| Matrix | Individual donor plasma (male and female) ("subject"), platelet-poor |
| aPTT Test Concentrations | Five concentrations: 1.0, 2.5, 5.0, 10.0, and 20.0 µg/mL bivalirudin |
| PT Test Concentrations | Four concentrations: 5.0, 10.0, 15.0, and 20.0 µg/mL bivalirudin |
| TT Test concentrations | Three concentrations: 0.5, 0.75, and 1.0 µg/mL bivalirudin |
| Number of subjects | 50 subjects (25 male and 25 female) |
| Equivalence criterion | 90% confidence intervals of the estimated ratio of geometric mean (RGM) of the parameter between the Test and the Reference (Test/Reference) will be within 0.90 to 1.11 (or 90.0% to 111.0%), original scale (−0.154 to +0.1054 natural log scale), inclusive for all coagulation parameters at all tested concentration levels |

The PT, aPTT, and TT measurements were conducted using in-vitro diagnostic (IVD) approved instrument applications provided by Siemens Healthcare Inc. for the BCS XP coagulation analyzer. Individual donor plasma samples (100 mL) were inspected visually for clotting, hemolysis, icterus, and lipemia or excess turbidity; plasma exhibiting any of these conditions were excluded from the study. Each plasma subject was used to prepare plasma samples spiked with either Test Drug or the Reference Drug at the target concentrations. A blank control (plasma only) and a vehicle control (0.9% sodium chloride injection) were also prepared.

The equivalence of the Test and the Reference products for the endpoints was tested using two one-sided tests at the 0.05 level of significance. SAS1 PROC MIXED procedure with model statements and variance covariance structure similar to Appendix E of Statistical Approaches to Establishing Bioequivalence (FDA Guidance for Industry 2001) was used to carry out the Two One-sided Test (TOST) procedure by fitting mixed effects models to the log-transformed aPTT, PT, and TT measures. The model had gender and formulation as fixed effects. A separate mixed effects model was used to analyze each measure at each dose using restricted maximum likelihood estimation, the Kenward and Roger method of calculating the degrees of freedom and the variance-covariance structure FA0(2). Formulation and subjects within each product were the random and repeated measures, respectively.

Table 17c summarizes the results of the equivalence analysis for all plasma samples; the results for the 90% confidence interval of the ratios of geometric means between the Test and the Reference are within are within 98.9% to 103.4% for all coagulation parameters at all tested concentration levels for all evaluable samples; thus the results meet the acceptance criterion of 90% to 111% (−0.1054 to +0.1054 on log scale) for all coagulation parameters at all tested concentration levels.

TABLE 17c

Equivalence Analysis of All Samples from Pharmacodynamic Study

| Parameter | Dose (µg/mL) | N | Geometric Mean Clotting Time (seconds) Test | Geometric Mean Clotting Time (seconds) Reference | Ratio of Geometric Means (90% CI) (%) |
|---|---|---|---|---|---|
| PT | 0† | 50 | 10.89 | 10.62 | 102.5 (102.2, 102.8) |
|  | 5.0 | 50 | 37.12 | 36.35 | 102.1 (100.9, 103.4) |
|  | 10.0 | 50 | 72.98 | 71.80 | 101.6 (100.6, 102.7) |
|  | 15.0 | 50 | 105.01 | 103.54 | 101.4 (100.3, 102.5) |
|  | 20.0 | 50 | 134.56 | 132.19 | 101.8 (100.8, 102.8) |
| aPTT | 0† | 50 | 26.17 | 25.41 | 103.0 (102.7, 103.3) |
|  | 1.0 | 50 | 55.33 | 55.11 | 100.4 (100.1, 100.7) |
|  | 2.5 | 50 | 70.99 | 70.41 | 100.8 (100.4, 101.2) |
|  | 5.0 | 50 | 87.25 | 86.80 | 100.5 (100.2, 100.9) |
|  | 10.0 | 50 | 108.46 | 108.46 | 100.0 (98.9, 101.2) |
|  | 20.0 | 50 | 139.41 | 138.16 | 100.9 (100.5, 101.3) |
| TT | 0† | 50 | 20.74 | 20.34 | 102.0 (101.4, 102.6) |
|  | 0.5 | 50 | 251.03 | 246.63 | 101.8 (100.9, 102.6) |
|  | 0.75 | 50 | 342.17 | 338.18 | 101.2 (100.0, 102.4) |
|  | 1.0 | 48* | 415.28 | 407.8 | 101.8 (100.7, 103.0) |

[1] SAS is a registered trademark of the SAS Institute Inc., Cary, NC.
N = number of subjects;
†Test and Reference correspond to the blank (plasma only) and the vehicle control (0.9% saline);
*two subjects yielded no measurable clotting time ("no clot", clotting time >500 sec) for all replicates of the test and reference drug samples; thus, clotting data were available for only 48 subjects control (0.9% saline)

The results of the in vitro pharmacodynamic study clearly demonstrate that exemplary formulations of this disclosure with degradant levels at or above its shelf life levels are equivalent to Angiomax for Injection in terms of its anticoagulant activity, as measured by PT, aPTT, and TT at all concentrations tested over the therapeutic range.

The invention claimed is:

1. A method of inhibiting blood clots in a patient in need thereof comprising intravenously administering to the patient a therapeutically effective amount of a ready-to-use liquid composition comprising about 5 mg/mL bivalirudin or a salt thereof, about 0.8 mg/mL sodium acetate, about 100 mg/mL PEG 400, and water and optionally, glacial acetic acid and/or sodium hydroxide, wherein
the ready-to-use liquid composition is prepared by a method that comprises mixing bivalirudin or salt thereof, sodium acetate, PEG 400, and water and optionally glacial acetic acid and/or sodium hydroxide to form the ready-to-use liquid composition,
the composition is stored at 2-8° C. prior to administration, and
the composition has a pH of from greater than 5.0 to 5.7.

2. The method of claim 1, wherein the sodium acetate is sodium acetate trihydrate.

3. The method of claim 1, wherein the composition has a pH of 5.1 to 5.4.

4. The method of claim 3, wherein the percentage of total impurities increases by no more than about 9% from the time of manufacture of the composition up to 12 months of storage at 5° C. as determined by high performance liquid chromatography at a wavelength of 215 nm.

5. The method of claim 1, wherein the bivalirudin is in the form of a trifluoroacetate salt.

6. The method of claim 1, wherein the composition has an osmolality of about 200 to about 600 mOsm/kg.

7. The method of claim 1, wherein the patient has heparin-induced thrombocytopenia (HIT) and/or heparin-induced thrombocytopenia and thrombosis syndrome (HITTS) and is undergoing percutaneous coronary intervention (PCI).

8. The method of claim 1, wherein the composition has not been reconstituted from a lyophilized composition or diluted from a liquid concentrate.

9. A method of inhibiting blood clots in a patient in need thereof comprising intravenously administering to the patient a therapeutically effective amount of a ready-to-use liquid composition comprising about 5 mg/mL bivalirudin or a salt thereof, about 0.8 mg/mL sodium acetate trihydrate, about 100 mg/mL PEG 400, and water, wherein
the ready-to-use liquid composition is prepared by a method that comprises mixing bivalirudin or salt thereof, sodium acetate, PEG 400, and water,
the composition does not comprise sodium chloride or dextrose, and
the composition has a pH of from greater than 5.0 to 5.7.

10. The method of claim 9, wherein the pH of the composition is about 5.25.

11. The method of claim 10, wherein the percentage of total impurities increases by no more than about 9% from the time of manufacture of the composition up to 12 months of storage at 5° C. as determined by high performance liquid chromatography at a wavelength of 215 nm.

12. The method of claim 10, wherein the composition is stored at 2-8° C. prior to administration.

13. The method of claim 10, wherein the bivalirudin is in the form of a trifluoroacetate salt.

14. The method of claim 10, wherein the patient has heparin-induced thrombocytopenia (HIT) and/or heparin-induced thrombocytopenia and thrombosis syndrome (HITTS) and is undergoing percutaneous coronary intervention (PCI).

15. The method of claim 10, wherein the composition has not been reconstituted from a lyophilized composition or diluted from a liquid concentrate.

16. A method of inhibiting blood clots in a patient in need thereof comprising intravenously administering to the patient a therapeutically effective amount of a ready-to-use liquid composition comprising about 5 mg/mL (free base basis) of bivalirudin trifluoroacetate, about 0.8 mg/mL sodium acetate trihydrate, about 100 mg/mL PEG 400, and water, wherein
the composition is prepared by mixing the bivalirudin trifluoroacetate, sodium acetate, PEG 400, and water,
the composition is free of sodium chloride and dextrose,
the composition has a pH of from greater than 5.0 to 5.7, and
the percentage of total impurities increases by no more than about 9% from the time of manufacture of the composition up to 12 months of storage at 5° C. as determined by high performance liquid chromatography at a wavelength of 215 nm.

17. The method of claim 16, wherein the pH of the composition is about 5.25.

18. The method of claim 16, wherein the composition is stored at 2-8° C. prior to administration.

19. The method of claim 16, wherein the patient has heparin-induced thrombocytopenia (HIT) and/or heparin-induced thrombocytopenia and thrombosis syndrome (HITTS) and is undergoing percutaneous coronary intervention (PCI).

20. The method of claim 16, wherein the composition has not been reconstituted from a lyophilized composition or diluted from a liquid concentrate.

21. The method of claim 1, wherein the composition has a pH of about 5.25.

* * * * *